(12) United States Patent
Arizti et al.

(10) Patent No.: US 11,166,856 B2
(45) Date of Patent: Nov. 9, 2021

(54) SENSOR DEVICES AND SYSTEMS FOR MONITORING THE BASIC NEEDS OF AN INFANT

(71) Applicant: The Procter & Gamble Company, Cincinnati, OH (US)

(72) Inventors: Blanca Arizti, Schmitten (DE); Mark Reidy, Geneva (CH)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/452,726

(22) Filed: Jun. 26, 2019

(65) Prior Publication Data

US 2020/0046574 A1 Feb. 13, 2020

Related U.S. Application Data

(63) Continuation of application No. 16/402,348, filed on May 3, 2019.

(60) Provisional application No. 62/723,179, filed on Aug. 27, 2018, provisional application No. 62/666,989, filed on May 4, 2018.

(51) Int. Cl.
| | | |
|---|---|---|
| *A61F 13/42* | (2006.01) | |
| *A61B 5/00* | (2006.01) | |
| *G06Q 10/08* | (2012.01) | |
| *G08B 21/18* | (2006.01) | |
| *G08B 21/20* | (2006.01) | |

(Continued)

(52) U.S. Cl.
CPC ............ *A61F 13/42* (2013.01); *A61B 5/0077* (2013.01); *A61B 5/7275* (2013.01); *G06Q 10/087* (2013.01); *G08B 21/18* (2013.01); *G08B 21/20* (2013.01); *A61B 5/002* (2013.01); *A61B 5/01* (2013.01); *A61B 5/11* (2013.01); *A61B 5/4809* (2013.01); *A61B 2503/04* (2013.01); *A61B 2562/0219* (2013.01); *A61F 2013/424* (2013.01); *A61F 2013/427* (2013.01)

(58) Field of Classification Search
CPC .. A61F 13/42; A61F 13/505; A61F 2013/421; A61F 2013/428; G06Q 10/087; A61B 5/68; A61B 5/6801; A61B 5/6802; A61B 5/6808; A61B 5/01; A61B 5/0077; A61B 5/7275; A61B 2503/04; A61B 2562/0219; G08B 21/18; G08B 21/20
See application file for complete search history.

(56) References Cited

U.S. PATENT DOCUMENTS

| 3,848,594 A | 11/1974 | Buell |
|---|---|---|
| 3,860,003 A | 1/1975 | Buell |

(Continued)

FOREIGN PATENT DOCUMENTS

| CN | 106725506 A | 5/2017 |
|---|---|---|
| EP | 0149880 | 5/1984 |

(Continued)

OTHER PUBLICATIONS

U.S. Appl. No. 16/402,514, filed May 3, 2019, Arizti, et al.

(Continued)

*Primary Examiner* — Andrew W Bee
(74) *Attorney, Agent, or Firm* — Brian M. Bolam

(57) ABSTRACT

Sensor devices and systems for monitoring the basic needs of an infant comprising feeding, sleeping, and/or voiding (urinating and/or defecating) are described herein.

9 Claims, 13 Drawing Sheets

(51) Int. Cl.
*A61B 5/01* (2006.01)
*A61B 5/11* (2006.01)

(56) References Cited

U.S. PATENT DOCUMENTS

| | | | |
|---|---|---|---|
| 3,911,173 A | 10/1975 | Sprague |
| 4,022,210 A | 5/1977 | Glassman |
| 4,265,245 A | 5/1981 | Glassman |
| 4,286,331 A | 8/1981 | Anderson |
| 4,515,595 A | 5/1985 | Kievit et al. |
| 4,554,662 A | 11/1985 | Suzuki |
| 4,573,986 A | 3/1986 | Minetola et al. |
| 4,662,875 A | 5/1987 | Hirotsu et al. |
| 4,681,793 A | 7/1987 | Linman et al. |
| 4,695,278 A | 9/1987 | Lawson |
| 4,699,622 A | 10/1987 | Toussant et al. |
| 4,710,189 A | 12/1987 | Lash |
| 4,785,996 A | 11/1988 | Ziecker et al. |
| 4,795,454 A | 1/1989 | Dragoo |
| 4,808,178 A | 2/1989 | Aziz et al. |
| 4,842,666 A | 6/1989 | Werenicz |
| 4,846,815 A | 7/1989 | Scripps |
| 4,894,060 A | 1/1990 | Nestegard |
| 4,908,803 A | 3/1990 | Rialan |
| 4,940,464 A | 7/1990 | Van Gompel et al. |
| 4,946,527 A | 8/1990 | Battrell |
| 4,963,140 A | 10/1990 | Robertson et al. |
| 4,977,906 A | 12/1990 | Di |
| 5,036,859 A | 8/1991 | Brown |
| 5,137,537 A | 8/1992 | Herron et al. |
| 5,151,092 A | 9/1992 | Buell et al. |
| 5,221,274 A | 6/1993 | Buell et al. |
| 5,242,436 A | 9/1993 | Weil et al. |
| 5,264,830 A | 11/1993 | Kline et al. |
| 5,354,289 A | 10/1994 | Mitchell et al. |
| 5,415,649 A | 5/1995 | Watanabe |
| 5,433,715 A | 7/1995 | Tanzer et al. |
| 5,469,145 A | 11/1995 | Johnson |
| 5,499,978 A | 3/1996 | Buell et al. |
| 5,507,736 A | 4/1996 | Clear et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,590,152 A | 12/1996 | Nakajima et al. |
| 5,607,414 A | 3/1997 | Richards et al. |
| 5,628,097 A | 5/1997 | Benson et al. |
| 5,700,254 A | 12/1997 | McDowall et al. |
| 5,709,222 A | 1/1998 | Davallou |
| 5,714,156 A | 2/1998 | Schmidt et al. |
| 5,817,087 A | 10/1998 | Takabayashi |
| 5,838,240 A | 11/1998 | Johnson |
| 5,865,823 A | 2/1999 | Curro |
| 5,902,222 A | 5/1999 | Wessman |
| 5,938,648 A | 8/1999 | LaVon et al. |
| 5,959,535 A | 9/1999 | Remsburg |
| 6,004,306 A | 12/1999 | Robles et al. |
| 6,160,198 A | 3/2000 | Roe et al. |
| 6,093,869 A | 7/2000 | Roe et al. |
| 6,121,509 A | 9/2000 | Ashraf et al. |
| 6,179,820 B1 | 1/2001 | Yernors |
| 6,203,496 B1 | 3/2001 | Gael et al. |
| 6,246,330 B1 | 6/2001 | Nielsen |
| 6,264,643 B1 | 7/2001 | Toyoda |
| 6,306,122 B1 | 10/2001 | Narawa |
| 6,372,951 B1 | 4/2002 | Ovanesyan et al. |
| 6,384,296 B1 | 5/2002 | Roe et al. |
| 6,432,098 B1 | 8/2002 | Kline et al. |
| 6,501,002 B1 | 12/2002 | Roe et al. |
| 6,534,149 B1 | 3/2003 | Daley et al. |
| 6,583,722 B2 | 6/2003 | Jeutter |
| 6,603,403 B2 | 8/2003 | Jeutter et al. |
| 6,609,068 B2 | 8/2003 | Cranley |
| 6,617,488 B1 | 9/2003 | Springer et al. |
| 6,632,504 B1 | 10/2003 | Gillespie et al. |
| 6,645,190 B1 | 11/2003 | Olson et al. |
| 6,645,569 B1 | 11/2003 | Cramer et al. |
| 6,761,711 B1 | 7/2004 | Fletcher et al. |
| 6,817,994 B2 | 11/2004 | Popp et al. |
| 6,840,928 B2 | 1/2005 | Datta et al. |
| 6,849,067 B2 | 2/2005 | Fletcher et al. |
| 6,863,933 B2 | 3/2005 | Cramer et al. |
| 6,893,426 B1 | 5/2005 | Popp et al. |
| 6,946,585 B2 | 9/2005 | London Brown |
| 6,953,452 B2 | 10/2005 | Popp et al. |
| 6,969,377 B2 | 11/2005 | Koele et al. |
| 7,002,054 B2 | 2/2006 | Allen et al. |
| 7,049,969 B2 | 5/2006 | Tamai |
| 7,112,621 B2 | 9/2006 | Rohrbaugh et al. |
| 7,145,053 B1 | 12/2006 | Emenike |
| 7,156,833 B2 | 1/2007 | Courure-Dorschner et al. |
| 7,174,774 B2 | 2/2007 | Pawar |
| 7,201,744 B2 | 4/2007 | Van Gompel et al. |
| 7,241,627 B2 | 7/2007 | Wilhelm et al. |
| 7,250,547 B1 | 7/2007 | Hofmeister et al. |
| 7,295,125 B2 | 11/2007 | Gabriel |
| 7,355,090 B2 | 4/2008 | Alex et al. |
| 7,394,391 B2 | 7/2008 | Long |
| 7,410,479 B2 | 8/2008 | Hoshino |
| 7,449,614 B2 | 11/2008 | Alex |
| 7,477,156 B2 | 1/2009 | Long et al. |
| 7,489,252 B2 | 2/2009 | Long et al. |
| 7,497,851 B2 | 3/2009 | Koele et al. |
| 7,498,478 B2 | 3/2009 | Long et al. |
| 7,504,550 B2 | 3/2009 | Tippey et al. |
| 7,524,195 B2 | 4/2009 | Alex et al. |
| 7,527,615 B2 | 5/2009 | Roe |
| 7,537,832 B2 | 5/2009 | Carlucci et al. |
| 7,569,039 B2 | 8/2009 | Matsuda |
| 7,595,734 B2 | 9/2009 | Long et al. |
| 7,642,396 B2 | 1/2010 | Alex et al. |
| 7,649,125 B2 | 1/2010 | Ales et al. |
| 7,659,815 B2 | 2/2010 | Cohen et al. |
| 7,667,806 B2 | 2/2010 | Kim et al. |
| 7,682,349 B2 | 3/2010 | Popp et al. |
| 7,700,820 B2 | 4/2010 | Tippey et al. |
| 7,700,821 B2 | 4/2010 | Alex et al. |
| 7,737,322 B2 | 6/2010 | Alex et al. |
| 7,744,579 B2 | 6/2010 | Langdon |
| 7,753,691 B2 | 7/2010 | Ales et al. |
| 7,760,101 B2 | 7/2010 | Alex et al. |
| 7,786,341 B2 | 8/2010 | Schneider et al. |
| 7,789,869 B2 | 9/2010 | Berland et al. |
| 7,803,319 B2 | 9/2010 | Yang et al. |
| 7,812,731 B2 | 10/2010 | Benza et al. |
| 7,834,235 B2 | 11/2010 | Long et al. |
| 7,835,925 B2 | 11/2010 | Roe et al. |
| 7,846,383 B2 | 12/2010 | Song |
| 7,850,470 B2 | 12/2010 | Ales et al. |
| 7,855,653 B2 | 12/2010 | Rondoni et al. |
| 7,862,550 B2 | 1/2011 | Koele et al. |
| 7,879,392 B2 | 2/2011 | Wenzel et al. |
| 7,956,754 B2 | 4/2011 | Long |
| 7,946,869 B2 | 5/2011 | Ales et al. |
| 7,973,210 B2 | 7/2011 | Long et al. |
| 7,977,529 B2 | 7/2011 | Berman et al. |
| 8,007,485 B2 | 8/2011 | Popp et al. |
| 8,044,258 B2 | 10/2011 | Hietpas |
| 8,053,624 B2 | 11/2011 | Propp |
| 8,053,625 B2 | 11/2011 | Nhan et al. |
| 8,057,454 B2 | 11/2011 | Long et al. |
| 8,058,194 B2 | 11/2011 | Nhan et al. |
| 8,101,813 B2 | 1/2012 | Ales et al. |
| 8,111,165 B2 | 2/2012 | Ortega et al. |
| 8,115,643 B2 | 2/2012 | Wada et al. |
| 8,172,982 B2 | 5/2012 | Ales et al. |
| 8,173,380 B2 | 5/2012 | Yang et al. |
| 8,183,876 B2 | 5/2012 | Wada et al. |
| 8,196,270 B2 | 6/2012 | Mandzsu |
| 8,196,809 B2 | 6/2012 | Thorstensson |
| 8,207,394 B2 | 6/2012 | Feldkamp et al. |
| 8,215,973 B2 | 7/2012 | Ales et al. |
| 8,222,476 B2 | 7/2012 | Song et al. |
| 8,237,572 B2 | 8/2012 | Clement et al. |

(56) References Cited

U.S. PATENT DOCUMENTS

| | | |
|---|---|---|
| 8,248,249 B2 | 8/2012 | Clement et al. |
| 8,264,362 B2 | 9/2012 | Ales et al. |
| 8,274,393 B2 | 9/2012 | Ales et al. |
| 8,299,317 B2 | 10/2012 | Tippey et al. |
| 8,304,598 B2 | 11/2012 | Masbacher et al. |
| 8,314,284 B1 | 11/2012 | Novello |
| 8,334,226 B2 | 12/2012 | Nhan et al. |
| 8,334,425 B2 | 12/2012 | Ales et al. |
| 8,338,659 B2 | 12/2012 | Collins et al. |
| 8,350,694 B1 | 1/2013 | Trundle |
| 8,361,048 B2 | 1/2013 | Kuen et al. |
| 8,372,052 B2 | 2/2013 | Popp et al. |
| 8,372,242 B2 | 2/2013 | Ales et al. |
| 8,372,766 B2 | 2/2013 | Nhan et al. |
| 8,378,167 B2 | 2/2013 | Allen et al. |
| 8,381,536 B2 | 2/2013 | Nhan et al. |
| 8,384,378 B2 | 2/2013 | Feldkamp et al. |
| 8,395,014 B2 | 3/2013 | Helmer et al. |
| 8,416,088 B2 | 4/2013 | Ortega et al. |
| 8,431,766 B1 | 4/2013 | Lonero |
| 8,440,877 B2 | 5/2013 | Collins et al. |
| 8,452,388 B2 | 5/2013 | Feldkamp et al. |
| 8,471,715 B2 | 6/2013 | Solazzo et al. |
| 8,507,746 B2 | 8/2013 | Ong et al. |
| 8,518,009 B2 | 8/2013 | Saito |
| 8,518,010 B2 | 8/2013 | Kuwano |
| 8,546,639 B2 | 10/2013 | Wada et al. |
| 8,563,801 B2 | 10/2013 | Berland et al. |
| 8,570,175 B2 | 10/2013 | Rahimi |
| 8,579,876 B2 | 11/2013 | Popp et al. |
| 8,604,268 B2 | 12/2013 | Cohen et al. |
| 8,623,292 B2 | 1/2014 | Song et al. |
| 8,628,506 B2 | 1/2014 | Alex, III et al. |
| 8,882,731 B2 | 1/2014 | Suzuki et al. |
| 8,642,832 B2 | 2/2014 | Ales et al. |
| 8,697,933 B2 | 4/2014 | Alex et al. |
| 8,697,934 B2 | 4/2014 | Nhan et al. |
| 8,697,935 B2 | 4/2014 | Daanen |
| 8,698,641 B2 | 4/2014 | Abrham et al. |
| 8,742,198 B2 | 6/2014 | Wei et al. |
| 8,747,379 B2 | 6/2014 | Fletcher et al. |
| 8,773,117 B2 | 7/2014 | Feldkamp et al. |
| 8,779,785 B2 | 7/2014 | Wada et al. |
| 8,785,716 B2 | 7/2014 | Schafer et al. |
| 8,816,149 B2 | 8/2014 | Richardson et al. |
| 8,866,052 B2 | 10/2014 | Nhan et al. |
| 8,866,624 B2 | 10/2014 | Ales et al. |
| 8,884,769 B2 | 11/2014 | Novak |
| 8,889,944 B2 | 11/2014 | Abraham et al. |
| 8,920,731 B2 | 12/2014 | Nhan et al. |
| 8,933,291 B2 | 1/2015 | Wei et al. |
| 8,933,292 B2 | 1/2015 | Abraham et al. |
| 8,962,909 B2 | 2/2015 | Groosman et al. |
| 8,975,465 B2 | 3/2015 | Hong et al. |
| 8,978,452 B2 | 3/2015 | Johnson et al. |
| 8,988,231 B2 | 3/2015 | Chen |
| 9,018,434 B2 | 4/2015 | Ruman |
| 9,018,435 B2 | 4/2015 | Kawashima |
| 9,034,593 B2 | 5/2015 | Martin et al. |
| 9,070,060 B2 | 6/2015 | Forster |
| 9,072,632 B2 | 7/2015 | Lavon |
| 9,072,634 B2 | 7/2015 | Hundorf et al. |
| 9,168,185 B2 | 10/2015 | Berland et al. |
| 9,211,218 B2 | 12/2015 | Rinnert et al. |
| 9,295,593 B2 | 3/2016 | Van Malderen |
| 9,301,884 B2 | 4/2016 | Shah et al. |
| 9,314,381 B2 | 4/2016 | Curran et al. |
| 9,317,913 B2 | 4/2016 | Carney |
| 9,380,977 B2 | 7/2016 | Abir |
| 9,402,771 B2 | 8/2016 | Carney et al. |
| 9,421,137 B2 | 8/2016 | LaVon et al. |
| 9,545,342 B2 * | 1/2017 | Cretu-Petra ............ A61F 13/42 |
| 9,585,795 B2 | 3/2017 | Boase et al. |
| 10,702,705 B2 | 7/2020 | Malchano |
| 2002/0021220 A1 | 2/2002 | Dreyer |
| 2002/0070864 A1 | 6/2002 | Jeutter et al. |
| 2003/0105190 A1 | 6/2003 | Diehl et al. |
| 2003/0148684 A1 | 8/2003 | Cramer et al. |
| 2003/0208133 A1 | 11/2003 | Mault |
| 2004/0064114 A1 | 4/2004 | David |
| 2004/0106202 A1 | 6/2004 | Zainiev et al. |
| 2004/0127867 A1 | 7/2004 | Odorzynski et al. |
| 2004/0127878 A1 | 7/2004 | Olson |
| 2004/0220538 A1 | 11/2004 | Panopoulos |
| 2004/0236302 A1 | 11/2004 | Wilhelm et al. |
| 2004/0254549 A1 | 12/2004 | Olson et al. |
| 2005/0008839 A1 | 1/2005 | Cramer et al. |
| 2005/0033250 A1 | 2/2005 | Collette |
| 2005/0065487 A1 | 3/2005 | Graef et al. |
| 2005/0099294 A1 | 5/2005 | Bogner |
| 2005/0107763 A1 | 5/2005 | Matsuda |
| 2005/0124947 A1 | 6/2005 | Fernfors |
| 2005/0137542 A1 | 6/2005 | Underhill et al. |
| 2005/0156744 A1 | 7/2005 | Pires |
| 2005/0195085 A1 | 9/2005 | Cretu-Petra |
| 2006/0058745 A1 | 3/2006 | Pires |
| 2006/0061477 A1 | 3/2006 | Yeh |
| 2006/0069362 A1 | 3/2006 | Odorzynski |
| 2006/0195068 A1 | 8/2006 | Lawando |
| 2006/0222675 A1 | 10/2006 | Sabnis et al. |
| 2006/0224135 A1 | 10/2006 | Beck |
| 2006/0229578 A1 | 10/2006 | Roe |
| 2006/0264861 A1 | 11/2006 | Lavon |
| 2007/0044805 A1 | 3/2007 | Wedler |
| 2007/0046482 A1 | 3/2007 | Chan |
| 2007/0055210 A1 | 3/2007 | Kao |
| 2007/0100666 A1 | 5/2007 | Stivoric et al. |
| 2007/0142797 A1 | 6/2007 | Long et al. |
| 2007/0156106 A1 | 7/2007 | Klofta |
| 2007/0185467 A1 | 8/2007 | Klofta et al. |
| 2007/0233027 A1 | 10/2007 | Roe et al. |
| 2007/0252710 A1 | 11/2007 | Long |
| 2007/0252711 A1 | 11/2007 | Long et al. |
| 2007/0252713 A1 | 11/2007 | Rondoni et al. |
| 2007/0255241 A1 | 11/2007 | Weber et al. |
| 2007/0255242 A1 | 11/2007 | Ales et al. |
| 2007/0282286 A1 | 12/2007 | Collins |
| 2007/0287975 A1 | 12/2007 | Fujimoto |
| 2008/0021423 A1 | 1/2008 | Kiofta |
| 2008/0021428 A1 | 1/2008 | Klofta et al. |
| 2008/0052030 A1 | 2/2008 | Olson et al. |
| 2008/0054408 A1 | 3/2008 | Tippey et al. |
| 2008/0057693 A1 | 3/2008 | Tippey et al. |
| 2008/0058740 A1 | 3/2008 | Sullivan et al. |
| 2008/0058741 A1 | 3/2008 | Long et al. |
| 2008/0058742 A1 | 3/2008 | Ales |
| 2008/0074274 A1 | 3/2008 | Hu |
| 2008/0082063 A1 | 4/2008 | Ales |
| 2008/0132859 A1 | 6/2008 | Pires |
| 2008/0147031 A1 | 6/2008 | Long et al. |
| 2008/0208155 A1 | 8/2008 | Lavon |
| 2008/0218334 A1 | 9/2008 | Pitchers |
| 2008/0234644 A1 | 9/2008 | Hansson et al. |
| 2008/0266117 A1 | 10/2008 | Song et al. |
| 2008/0266122 A1 | 10/2008 | Ales et al. |
| 2008/0266123 A1 | 10/2008 | Ales |
| 2008/0269702 A1 | 10/2008 | Ales |
| 2008/0269707 A1 | 10/2008 | Song |
| 2008/0300559 A1 | 12/2008 | Gustafson |
| 2008/0312622 A1 | 12/2008 | Hundorf et al. |
| 2009/0058072 A1 | 3/2009 | Weber et al. |
| 2009/0062756 A1 | 3/2009 | Long et al. |
| 2009/0124990 A1 | 5/2009 | Feldkamp et al. |
| 2009/0155753 A1 | 6/2009 | Ales et al. |
| 2009/0198202 A1 | 8/2009 | Nedestam |
| 2009/0275908 A1 | 11/2009 | Song |
| 2009/0326409 A1 | 12/2009 | Cohen et al. |
| 2009/0326504 A1 | 12/2009 | Kaneda |
| 2010/0013778 A1 | 1/2010 | Liu |
| 2010/0030173 A1 | 2/2010 | Song et al. |
| 2010/0125949 A1 * | 5/2010 | Stebbing ............... A47C 21/044 5/423 |
| 2010/0145294 A1 | 6/2010 | Song et al. |
| 2010/0152688 A1 | 6/2010 | Handwerker et al. |

(56) References Cited

U.S. PATENT DOCUMENTS

| | | |
|---|---|---|
| 2010/0159599 A1 | 6/2010 | Song et al. |
| 2010/0159611 A1 | 6/2010 | Song et al. |
| 2010/0160882 A1 | 6/2010 | Lowe |
| 2010/0164733 A1 | 7/2010 | Ales et al. |
| 2010/0168694 A1 | 7/2010 | Gakhar et al. |
| 2010/0168702 A1 | 7/2010 | Ales et al. |
| 2010/0241094 A1 | 9/2010 | Sherron |
| 2010/0277324 A1 | 11/2010 | Yeh |
| 2011/0004175 A1 | 1/2011 | Veith |
| 2011/0251038 A1 | 10/2011 | Lavon |
| 2011/0298597 A1 | 12/2011 | Kaihori |
| 2012/0310191 A1 | 2/2012 | LaVon et al. |
| 2012/0061016 A1 | 3/2012 | LaVon |
| 2012/0109087 A1* | 5/2012 | Abraham ............... A61F 13/42 604/361 |
| 2012/0116337 A1 | 5/2012 | Ales |
| 2012/0116343 A1 | 5/2012 | Yoshioka |
| 2012/0130330 A1 | 5/2012 | Wilson et al. |
| 2012/0157947 A1 | 6/2012 | Nhan |
| 2012/0161960 A1 | 6/2012 | Cheng |
| 2012/0172824 A1 | 7/2012 | Khaknazarov |
| 2012/0190956 A1 | 7/2012 | Connolly |
| 2012/0206265 A1 | 8/2012 | Solazzo |
| 2012/0225200 A1 | 9/2012 | Mandzsu |
| 2012/0245541 A1 | 9/2012 | Suzuki |
| 2012/0245542 A1 | 9/2012 | Suzuki et al. |
| 2012/0256750 A1 | 10/2012 | Novak |
| 2012/0282681 A1 | 11/2012 | Teixeira et al. |
| 2012/0299721 A1 | 11/2012 | Jones |
| 2012/0310190 A1 | 12/2012 | LaVon et al. |
| 2012/0310192 A1 | 12/2012 | Suzuki et al. |
| 2012/0323194 A1 | 12/2012 | Suzuki et al. |
| 2013/0012896 A1 | 1/2013 | Suzuki et al. |
| 2013/0018340 A1 | 1/2013 | Abraham et al. |
| 2013/0023786 A1 | 1/2013 | Mani et al. |
| 2013/0041334 A1 | 2/2013 | Prioleau |
| 2013/0076509 A1 | 3/2013 | Ahn |
| 2013/0110061 A1 | 5/2013 | Abraham et al. |
| 2013/0110063 A1 | 5/2013 | Abraham |
| 2013/0110075 A1 | 5/2013 | Mukai |
| 2013/0131618 A1 | 5/2013 | Abraham et al. |
| 2013/0151186 A1 | 6/2013 | Feldkamp |
| 2013/0161380 A1 | 6/2013 | Joyce et al. |
| 2013/0162402 A1 | 6/2013 | Amann et al. |
| 2013/0162403 A1 | 6/2013 | Stiemer et al. |
| 2013/0162404 A1 | 6/2013 | Stiemer et al. |
| 2013/0165809 A1 | 6/2013 | Abir |
| 2013/0211363 A1 | 8/2013 | LaVon et al. |
| 2013/0261409 A1 | 10/2013 | Pathak |
| 2013/0303867 A1 | 11/2013 | Elfstrom et al. |
| 2013/0307570 A1 | 11/2013 | Bosae et al. |
| 2013/0310796 A1 | 11/2013 | Zink |
| 2013/0321007 A1 | 12/2013 | Elfstrom et al. |
| 2013/0324955 A1 | 12/2013 | Wong et al. |
| 2013/0338623 A1 | 12/2013 | Kinoshita |
| 2014/0005020 A1 | 1/2014 | LaVon et al. |
| 2014/0005622 A1 | 1/2014 | Wirtz et al. |
| 2014/0014716 A1 | 1/2014 | Joyce et al. |
| 2014/0015644 A1 | 1/2014 | Amann et al. |
| 2014/0015645 A1 | 1/2014 | Stiemer et al. |
| 2014/0022058 A1 | 1/2014 | Stiemer et al. |
| 2014/0062663 A1 | 3/2014 | Bourilkov et al. |
| 2014/0121473 A1 | 5/2014 | Banet et al. |
| 2014/0121487 A1 | 5/2014 | Faybishenko et al. |
| 2014/0152442 A1 | 6/2014 | Liu |
| 2014/0155850 A1 | 6/2014 | Shah et al. |
| 2014/0155851 A1 | 6/2014 | Ales et al. |
| 2014/0163502 A1 | 6/2014 | Arizti et al. |
| 2014/0188063 A1 | 7/2014 | Nhan et al. |
| 2014/0198203 A1 | 7/2014 | Vardi |
| 2014/0200538 A1 | 7/2014 | Euliano et al. |
| 2014/0241954 A1 | 8/2014 | Phillips et al. |
| 2014/0242613 A1 | 8/2014 | Takeuchi et al. |
| 2014/0242715 A1 | 8/2014 | Nhan et al. |
| 2014/0244644 A1 | 8/2014 | Maschinchi et al. |
| 2014/0266736 A1 | 9/2014 | Cretu-Petra |
| 2014/0292520 A1 | 10/2014 | Carney et al. |
| 2014/0306814 A1* | 10/2014 | Ricci ..................... H04W 4/21 340/425.5 |
| 2014/0033442 A1 | 11/2014 | Carney |
| 2014/0329212 A1 | 11/2014 | Ruman et al. |
| 2014/0329213 A1 | 11/2014 | Ruman et al. |
| 2014/0363354 A1 | 12/2014 | Phillips et al. |
| 2014/0371702 A1 | 12/2014 | Bosae et al. |
| 2015/0025347 A1 | 1/2015 | Song |
| 2015/0042489 A1 | 2/2015 | LaVon |
| 2015/0045608 A1* | 2/2015 | Karp ..................... A47D 15/008 600/28 |
| 2015/0112202 A1 | 4/2015 | Abir |
| 2015/0130637 A1 | 5/2015 | Sengstaken, Jr. |
| 2015/0143881 A1 | 5/2015 | Raut et al. |
| 2015/0150732 A1 | 6/2015 | Abir |
| 2015/0157512 A1 | 6/2015 | Abir |
| 2015/0206151 A1 | 7/2015 | Carney et al. |
| 2015/0209193 A1 | 7/2015 | Ying et al. |
| 2015/0223755 A1 | 8/2015 | Abir |
| 2015/0276656 A1 | 10/2015 | Striemer |
| 2015/0317684 A1 | 11/2015 | Abir |
| 2015/0359490 A1 | 12/2015 | Massey |
| 2016/0008182 A1 | 1/2016 | Prokopuk et al. |
| 2016/0051416 A1 | 2/2016 | Vartiainen et al. |
| 2016/0051417 A1 | 2/2016 | Chu |
| 2016/0067113 A1 | 3/2016 | Vartiainen et al. |
| 2016/0078716 A1 | 3/2016 | Goldman |
| 2016/0080841 A1 | 3/2016 | Bergstrom et al. |
| 2016/0113822 A1 | 4/2016 | Vartiainen et al. |
| 2016/0134497 A1 | 5/2016 | Hermansson et al. |
| 2016/0136014 A1 | 5/2016 | Arora et al. |
| 2016/0170776 A1 | 6/2016 | Bergstrom et al. |
| 2016/0235603 A1 | 8/2016 | Ehrnsperger et al. |
| 2016/0287073 A1 | 10/2016 | Pradeep |
| 2016/0292986 A1 | 10/2016 | Pradeep et al. |
| 2016/0293042 A1 | 10/2016 | Pradeep |
| 2016/0345914 A1 | 12/2016 | Jain |
| 2016/0374868 A1 | 12/2016 | Ettrup Hansen |
| 2017/0035622 A1 | 2/2017 | Wang |
| 2017/0108236 A1* | 4/2017 | Guan ..................... G05B 15/02 |
| 2017/0116484 A1 | 4/2017 | Johnson |
| 2017/0156594 A1 | 6/2017 | Stivoric |
| 2017/0224543 A1 | 8/2017 | Lavon |
| 2017/0224551 A1 | 8/2017 | Lavon |
| 2017/0252225 A1 | 9/2017 | Arizti et al. |
| 2017/0278373 A1 | 9/2017 | Ansley |
| 2017/0286977 A1* | 10/2017 | Allen ................. G06Q 30/0254 |
| 2018/0053396 A1* | 2/2018 | Greene ................. G08B 25/08 |
| 2018/0096290 A1* | 4/2018 | Awad ................. G06Q 30/0635 |
| 2018/0104114 A1 | 4/2018 | Pepin |
| 2018/0149635 A1 | 5/2018 | Abir |
| 2018/0204256 A1 | 7/2018 | Bifolco |
| 2019/0180341 A1* | 6/2019 | Matra ................. G06Q 30/0621 |
| 2019/0336353 A1 | 11/2019 | Arizti |
| 2020/0060885 A1 | 2/2020 | Arizti |
| 2020/0060886 A1 | 2/2020 | Arizti |
| 2020/0177848 A1 | 6/2020 | Arizti |

FOREIGN PATENT DOCUMENTS

| | | |
|---|---|---|
| EP | 1216673 | 10/2005 |
| EP | 1542635 | 4/2012 |
| EP | 2491899 | 7/2014 |
| GB | 2549099 A | 10/2017 |
| JP | 09187431 | 7/1997 |
| JP | 2002022687 | 1/2002 |
| JP | 2002143199 | 5/2002 |
| JP | 2003190209 | 7/2003 |
| JP | 2004230135 | 8/2004 |
| JP | 2006296566 | 11/2006 |
| WO | WO 95016746 | 6/1995 |
| WO | WO 99034841 | 7/1999 |
| WO | 0197466 A1 | 12/2001 |
| WO | WO 20050011491 A1 | 5/2005 |
| WO | WO 2010123364 | 10/2010 |
| WO | WO 2010123425 | 10/2010 |
| WO | WO 2011013874 | 2/2011 |

(56) References Cited

FOREIGN PATENT DOCUMENTS

| | | |
|---|---|---|
| WO | WO 2012084925 | 6/2012 |
| WO | WO 2012126507 | 9/2012 |
| WO | WO 2013003905 | 1/2013 |
| WO | WO 2013016765 | 2/2013 |
| WO | WO 2013061963 | 5/2013 |
| WO | WO 2013091707 | 6/2013 |
| WO | WO 2013091728 | 6/2013 |
| WO | WO 2013095222 | 6/2013 |
| WO | WO 2013095226 | 6/2013 |
| WO | WO 2013095230 | 6/2013 |
| WO | WO 2013095231 | 6/2013 |
| WO | WO 2013097899 | 7/2013 |
| WO | WO 2013181436 | 12/2013 |
| WO | WO 2013185419 | 12/2013 |
| WO | WO 2013189284 | 12/2013 |
| WO | WO 2014035302 | 3/2014 |
| WO | WO 2014035340 | 3/2014 |
| WO | WO 2014122169 | 8/2014 |
| WO | WO 2014137671 | 9/2014 |
| WO | WO 2014146693 | 9/2014 |
| WO | WO 2014146694 | 9/2014 |
| WO | WO 2014148957 | 9/2014 |
| WO | WO 2014177200 | 11/2014 |
| WO | WO 2014177203 | 11/2014 |
| WO | WO 2014177204 | 11/2014 |
| WO | WO 2014177205 | 11/2014 |
| WO | WO 2014178763 | 11/2014 |
| WO | WO 2014192978 | 12/2014 |
| WO | WO 2015003712 | 1/2015 |
| WO | WO 2015068124 | 5/2015 |
| WO | WO 2015102084 | 7/2015 |
| WO | WO 2015102085 | 7/2015 |
| WO | 2015127062 A1 | 8/2015 |
| WO | WO 20160164373 A1 | 10/2016 |
| WO | 2017217859 | 12/2017 |
| WO | WO 2018/216848 A1 | 11/2018 |

OTHER PUBLICATIONS http://www.goodmonit.com/.
PCT International Search Report, dated Aug. 16, 2019, 14 pages.
All Office Actions; U.S. Appl. No. 16/402,514.
Ail Office Actions, U.S. Appl. No. 16/402,348.
Ail Office Actions, U.S. Appl. No. 16/452,693.
Ail Office Actions, U.S. Appl. No. 16/452,712.
https://techcrunch.com/2017/04/30/monit/ (May 1, 2017).
PCT Search Report; PCT/US2019/030361, dated Aug. 16, 2019, 14 pages.
All Office Actions; U.S. Appl. No. 17/220,356.
U.S. Appl. No. 17/220,356, filed Apr. 1, 2021, to Blanca Arizti et al.

* cited by examiner

SENSOR DEVICES AND SYSTEMS FOR MONITORING THE BASIC NEEDS OF AN INFANT

FIELD OF THE DISCLOSURE

The present disclosure relates to sensor devices and systems for monitoring the basic needs of an infant comprising feeding, sleeping, and/or voiding (urinating and/or defecating).

BACKGROUND

Smart devices and systems for monitoring the care of infants and ageing adults are becoming more commonplace. Examples of such devices includes wetness sensors associated with diapers and adult incontinence products that can sense when urination occurs and then alert a caregiver that a product change is in order. Visual and audio monitoring devices are also employed for determining the location, activity of, and needs of an infant or adult patient.

Feeding is a critical function for continued health and life. However, tracking feeding typically involves feedback from the individual feeding, at least some caregiver input, and/or employment of sophisticated equipment. There is a need to easily and automatically sense feeding characteristics (e.g., time and/or intake volume) of an individual that is unable to provide useable feedback to a caregiver and without a caregiver having to track, monitor, and/or record the feeding characteristics.

Separate and apart from the need for an improved system for understanding feeding characteristics, there is also a need for improved systems and methods for monitoring multiple aspects of an infant's or patient's wellbeing. Known systems tend to be bulky, incorporate electronic components within mass produced disposable articles, and/or are complicated to use in busy lives. Various forms of the present disclosure address one or more of these identified needs.

SUMMARY

Forms of the present disclosure provide a system for monitoring the basic needs of an infant (or patient), including feeding, sleeping, and/or voiding. The system includes a data gathering module that includes a sensor device for temporary association with an absorbent article or clothing worn by the infant (or patient); a data processing module; and a communication module. The sensor device includes a sensor housing and a plurality of electronic components disposed on and/or within the sensor housing. The data processing unit is configured to receive sensor data from the sensor device and communicate information related to the sensor data to a communication module. The communication module includes a software application that enables information related to feeding, sleeping, and/or voiding to be displayed to a caregiver via a computer platform based on data comprising the sensor data. The information related to voiding can include a urination event, a bowel movement event, or simply a diaper change. The information related to feeding is derived from the sensor device, and can relate to breast feeding, bottle feeding, or both. The data gathering module can also comprise a camera to capture images of an infant or patient wearing a disposable absorbent article to which the sensor device is attached. An optional camera may comprise additional functionality, including environmental sensing and data processing (e.g., communicating data from the sensor device to a router for subsequent transmission of data via the internet). Systems of the present disclosure may employ multiple cameras. For example, cameras can be placed into several rooms of a house, with the video feeds from one or more of the cameras being communicated to a caregiver. The cameras may be able to detect the presence of a monitored individual through the location of the sensor device and/or via motion detection. In this scenario, only one of the cameras may be communicating data to a caregiver at any one time.

Systems of the present disclosure can further include a plurality of absorbent articles to which the sensor device can be attached to and detached from. In this form, the sensor becomes a multi-use sensor enabling a cost effective smart product that includes disposable components and a non-disposable component.

Forms of the present disclosure provide methods for monitoring the basic needs of an infant (or patient). The methods include the steps of providing a sensor device with instructions of how and where to attach the sensor device to a disposable absorbent article, providing a software application operable on a computer device that can display information based on data generated by the sensor device when the disposable absorbent article containing the sensor device is placed onto an infant/patient, and providing data processing for manipulating the data generated by the sensor device to transform or interpret the data generated by the sensor device to consumer understandable information related to feeding, sleeping, and/or voiding.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein.

DETAILED DESCRIPTION

Various non-limiting aspects of the present disclosure will now be described to provide an overall understanding of the principles of the structure, function, manufacture, and/or use of the subject matter disclosed herein. In the following detailed description, reference is made to the accompanying figures, which form a part hereof. In the figures, similar symbols may identify similar elements, unless context dictates otherwise. It will be readily understood that the aspects of the present disclosure, as generally described herein, and illustrated in the figures, can be arranged, substituted, combined, separated, and designed in a wide variety of different configurations, all of which are explicitly contemplated herein.

Figure 1:
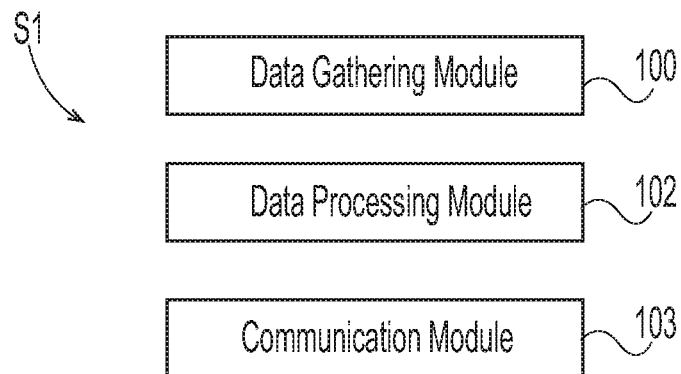
FIG. 1 is a schematic illustrating modules associated with systems of the present disclosure.

With reference to FIG. 1, exemplary systems S1 of the present disclosure generally include three elements: a data gathering module 100, a data processing module 102, and a communication module 103. The data gathering module includes a sensor device that can be associated with a disposable absorbent article or article of clothing worn by an infant or patient. Besides a sensor device worn with a disposable absorbent article, the data gathering module can comprise other sensor devices or equipment in proximity to the person wearing the sensor device. For example, the data gathering module may comprise a camera; an environmental sensor for sensing smoke, carbon monoxide, temperature, relative humidity; a motion sensor, an audio recorder, and the like. The data processing module can comprise data transmission, data storage, data interpretation, and/or data manipulation to transform the data from the data gathering module into consumer understandable information related to the wellbeing of an individual, including, for example, feeding, sleeping, and/or voiding. And the communication module comprises a software application for communicating (e.g., displaying) the consumer understandable information.

Figure 2:
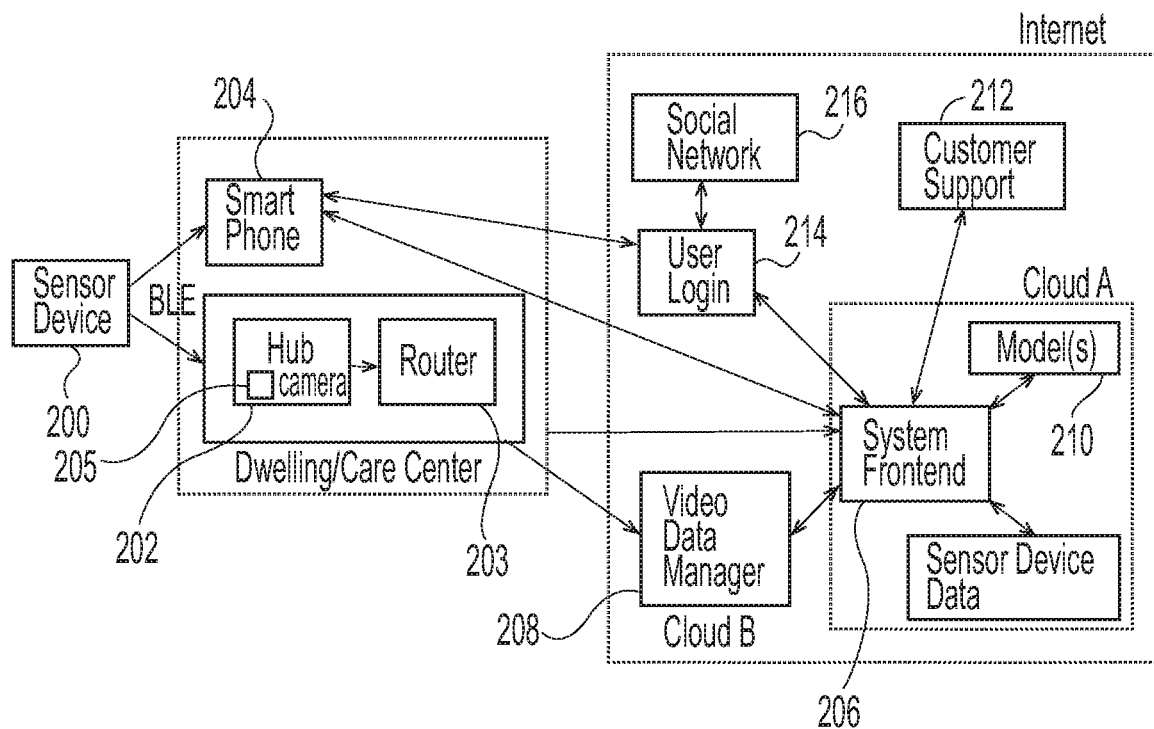
FIG. 2 is a schematic showing operational aspects of the sensor devices and systems of the present disclosure.

FIG. 2 is an exemplary schematic illustrating how sensor devices and systems of the present disclosure can operate. Two example operation modes are shown; one where the sensor device 200 is worn by an infant/patient that is located within a dwelling or care center 202 with wireless communication (e.g., Bluetooth low energy, 15.4, ad hoc mesh networks, and the like) conducted between sensor device 200 and a hub 202. And another where the infant/patient is located remotely (e.g., in a car or stroller) with wireless communication conducted between sensor device 200 and a smart device 204 (e.g., phone). Data and information from sensor device 200 is communicated via a router 203 or smart device 204 to a system frontend 206 for transforming the data and information to consumer usable information provided via a software application.

FIG. 2 shows additional optional aspects of systems of the present disclosure. Hub 202 may comprise a camera and other sensors for additional data gathering. Video streams and/or images can be communicated from the optional camera 205 to video data manager 208. It should be understood that while FIG. 2 shows separate data management systems for sensor device data located on Cloud A and for video/image data located on Cloud B, all of the data could be communicated with a single data management system.

Data management system Cloud A may contain one or more relationship models 210 to enable a primary account holder (e.g., mom or dad) to provide access to some or all of the data to secondary care providers (e.g., grandparent, nanny, daycare employee). By way of example only, the primary account holder receives video/image data, but does not provide access of the same to secondary care providers.

FIG. 2 shows optional online customer support 212. Customer support 212 can include a variety of functionality ranging from sensor device operational assistance to replenishment of disposable absorbent articles via an integrated eCommerce site.

FIG. 2 further shows alternative login portals 214 and 216. Login portal 214 is a standalone access for confirming the identity of an account holder that is seeking access to the data and information flowing from the sensor device and systems comprising the same. Login portal 216 represents an alternative access point through an existing network account—for example, a Google or Facebook account.

Descriptions of exemplary disposable absorbent articles to which the sensor device can be associated with is provided below, followed by a description of the system modules, a description of exemplary sensor device forms, and optional additional aspects of systems of the present disclosure.

I. Disposable Absorbent Articles

Figure 3:
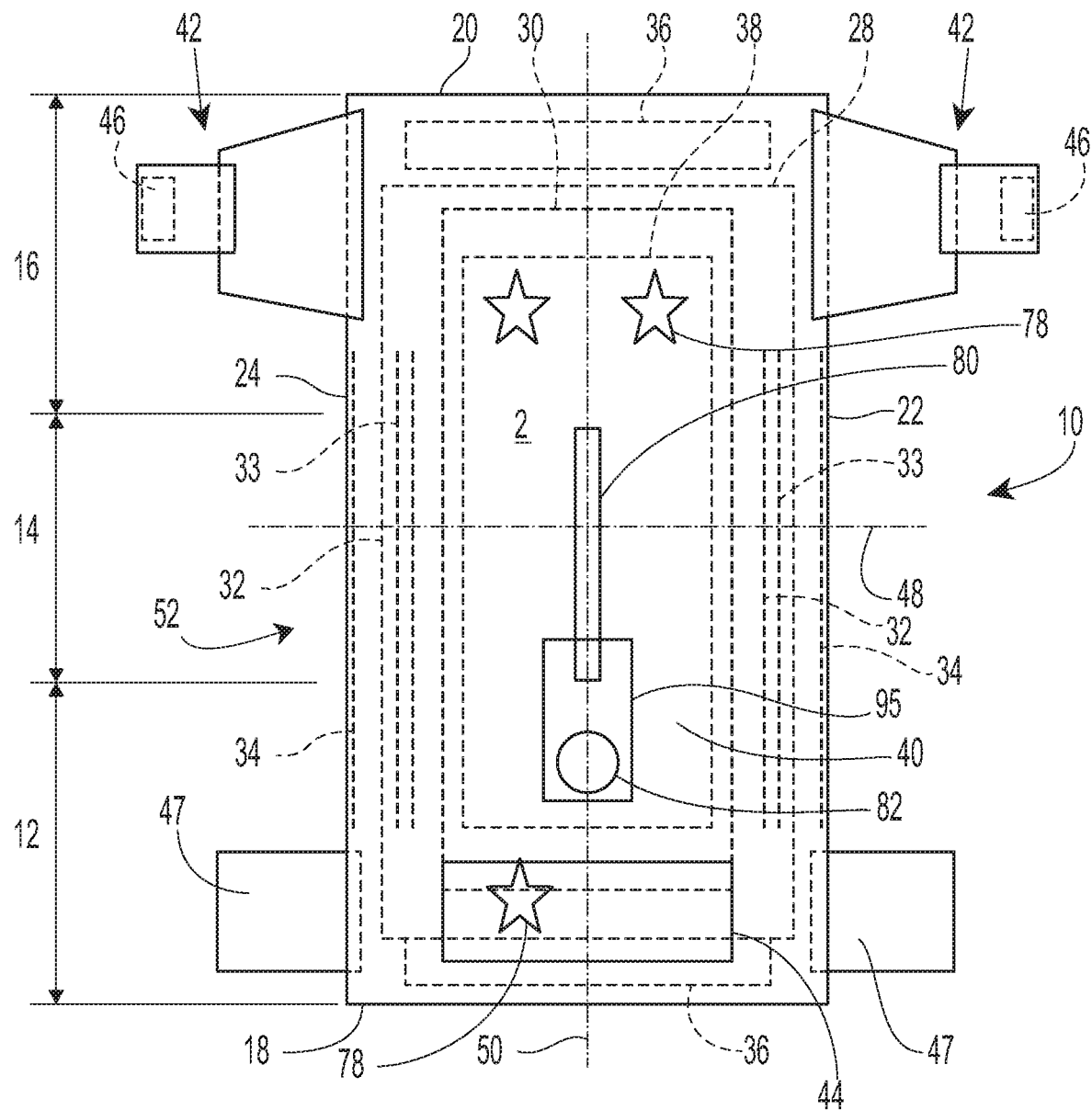
FIG. 3 is a plan view of an example absorbent article in the form of a taped diaper, garment-facing surface facing the viewer, in a flat laid-out state.
Figure 4:
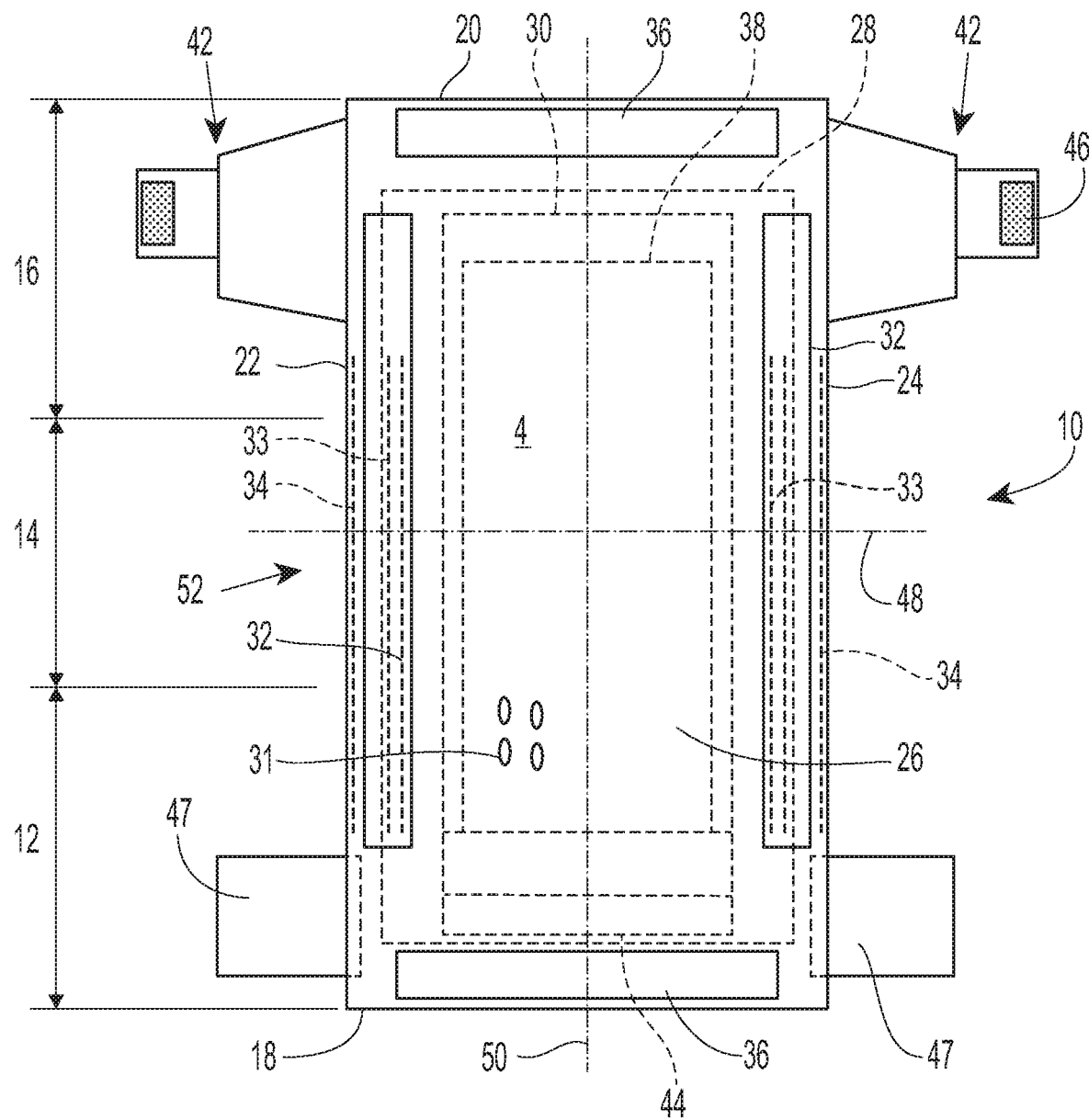
FIG. 4 is a plan view of the example absorbent article of FIG. 3, wearer-facing surface facing the viewer, in a flat laid-out state.
Figure 5:
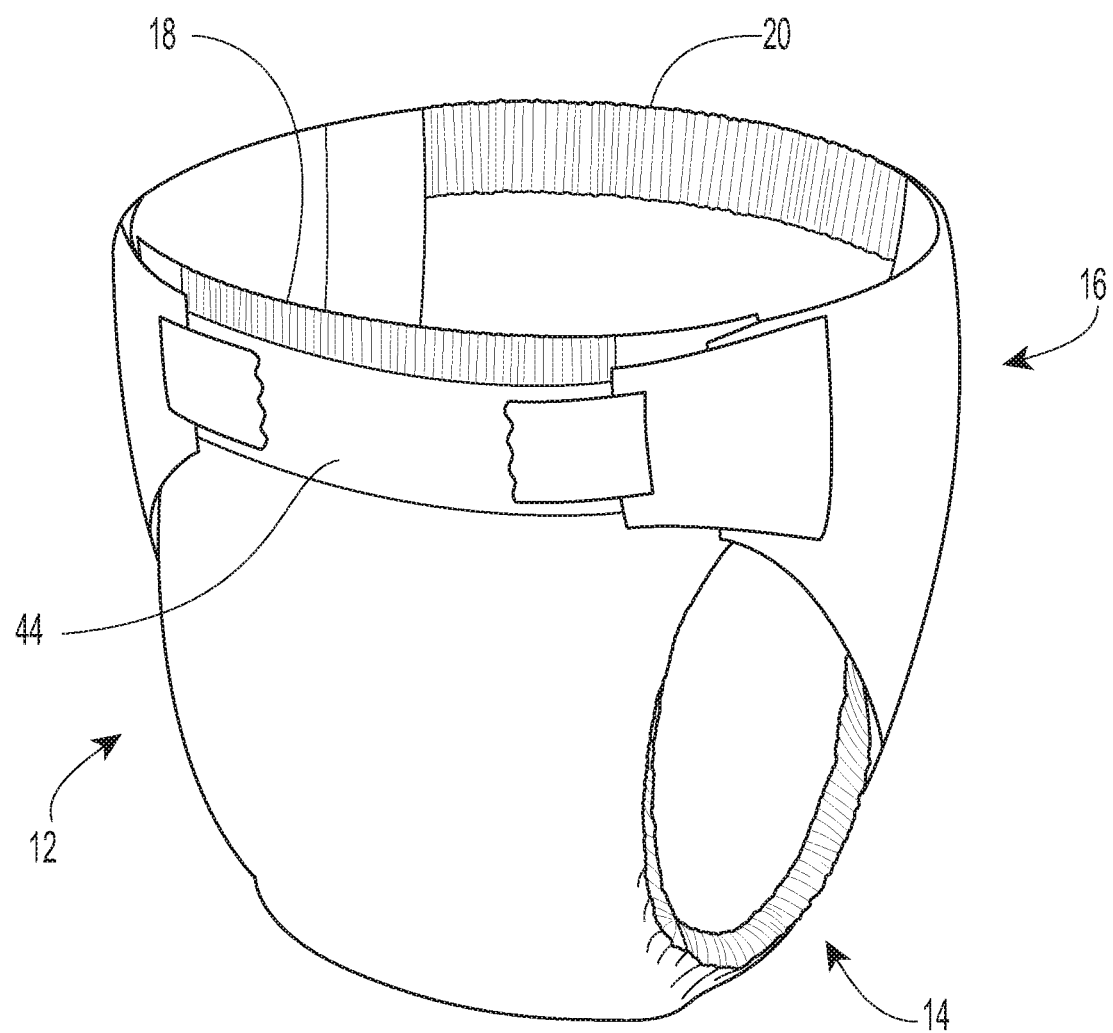
FIG. 5 is a front perspective view of the absorbent article of FIGS. 3 and 4 in a fastened position.

An exemplary disposable absorbent article 10 according to the present disclosure, shown in the form of a taped diaper, is represented in FIGS. 3-5. FIG. 3 is a plan view of the example absorbent article 10, garment-facing surface 2 facing the viewer in a flat, laid-out state (i.e., no elastic contraction). FIG. 4 is a plan view of the example absorbent article 10 of FIG. 3, wearer-facing surface 4 facing the viewer in a flat, laid-out state. FIG. 5 is a front perspective view of the absorbent article 10 of FIGS. 3 and 4 in a fastened configuration. The absorbent article 10 of FIGS. 3-5 is shown for illustration purposes only as the present disclosure may be used for making a wide variety of diapers, including adult incontinence products, pants, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front wait region 12, the crotch region 14, and the back waist region 16 may each be ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. An outer cover material 40, such as a nonwoven material, may cover a garment-facing side of the backsheet 28. The absorbent article 10 may comprise back ears 42 in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. The absorbent article 10 may have a central lateral (or transverse) axis 48 and a central longitudinal axis 50. The central lateral axis 48 extends perpendicular to the central longitudinal axis 50.

Figure 6:
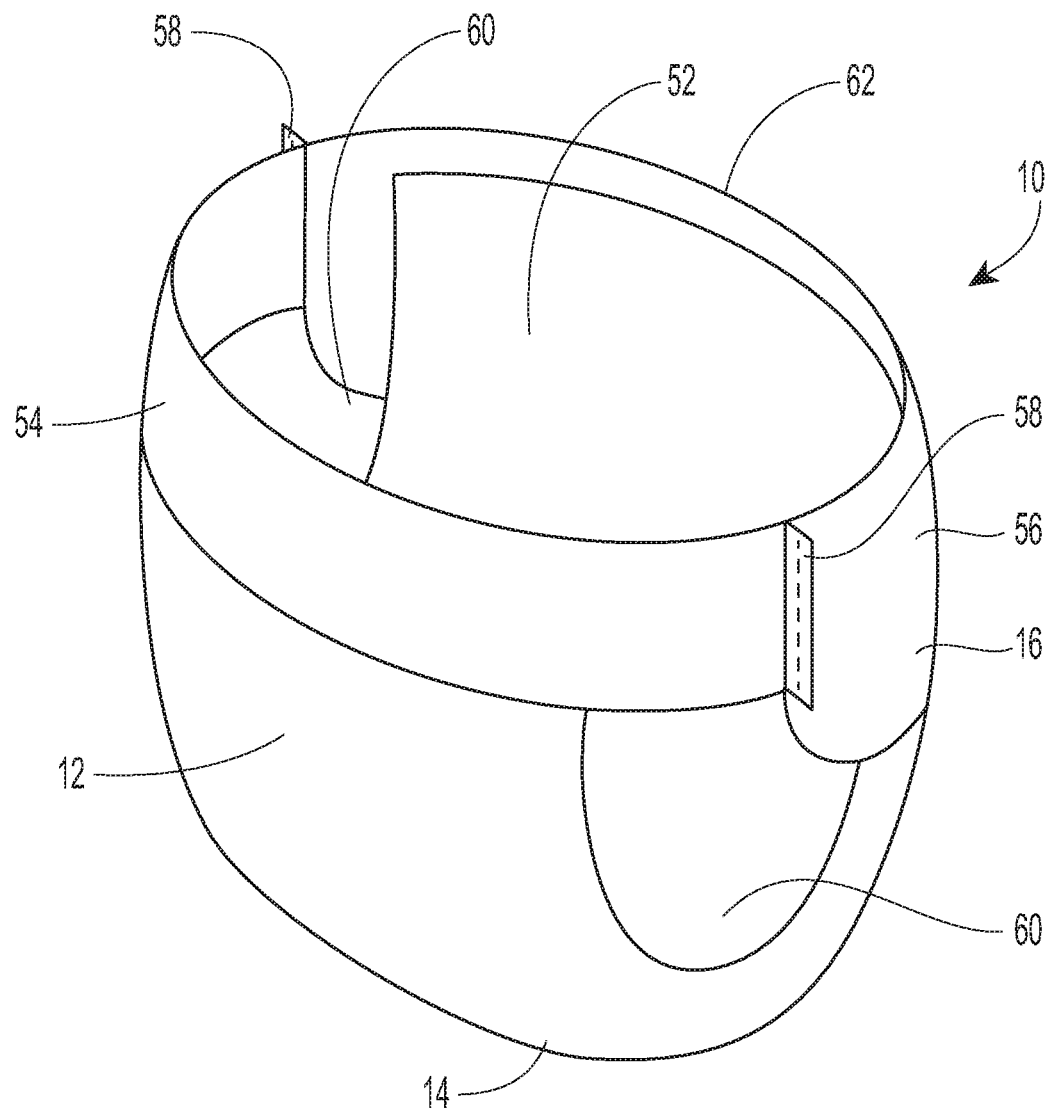
FIG. 6 is a front perspective view of an absorbent article in the form of a pant.
Figure 7:
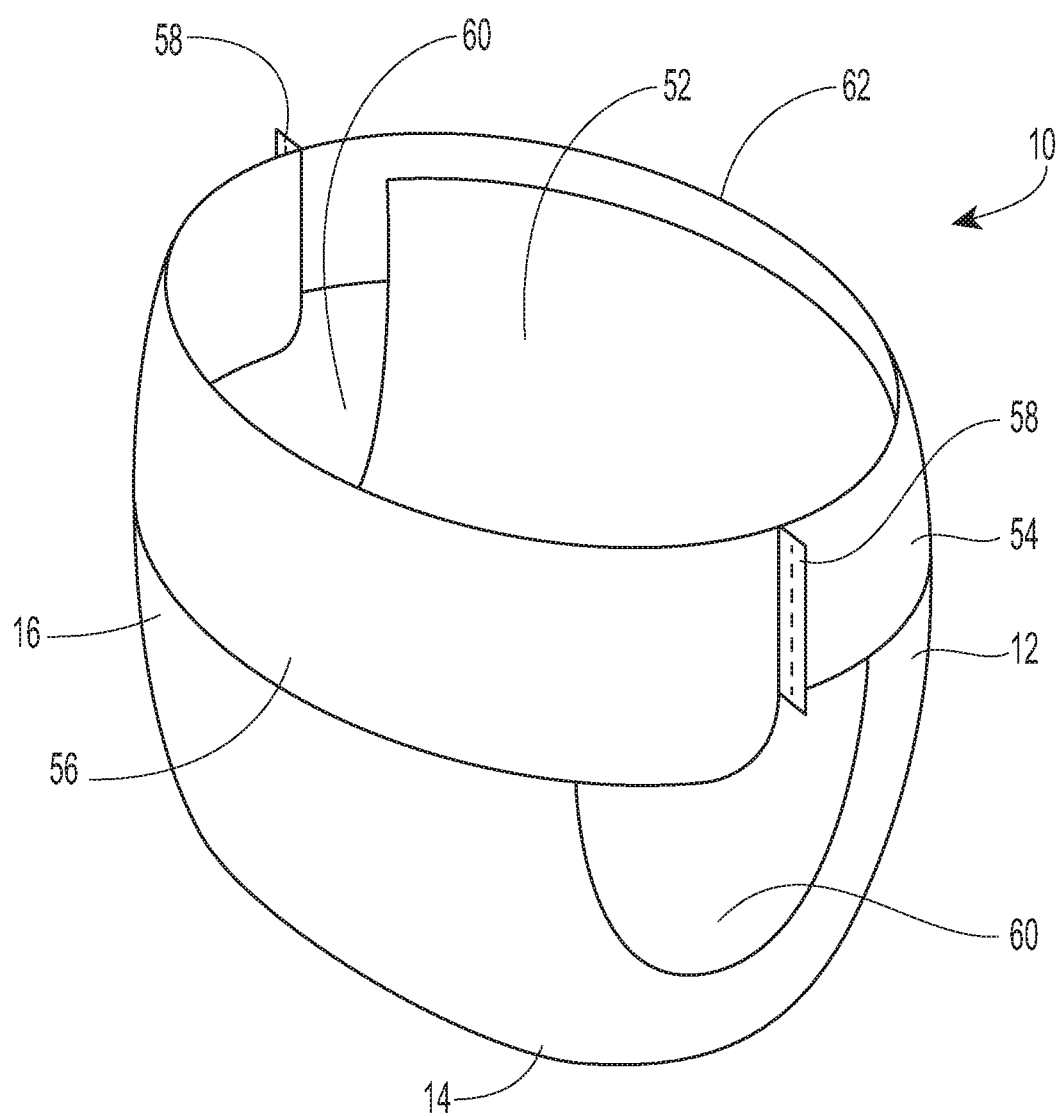
FIG. 7 is a rear perspective view of the absorbent article of FIG. 6.
Figure 8:
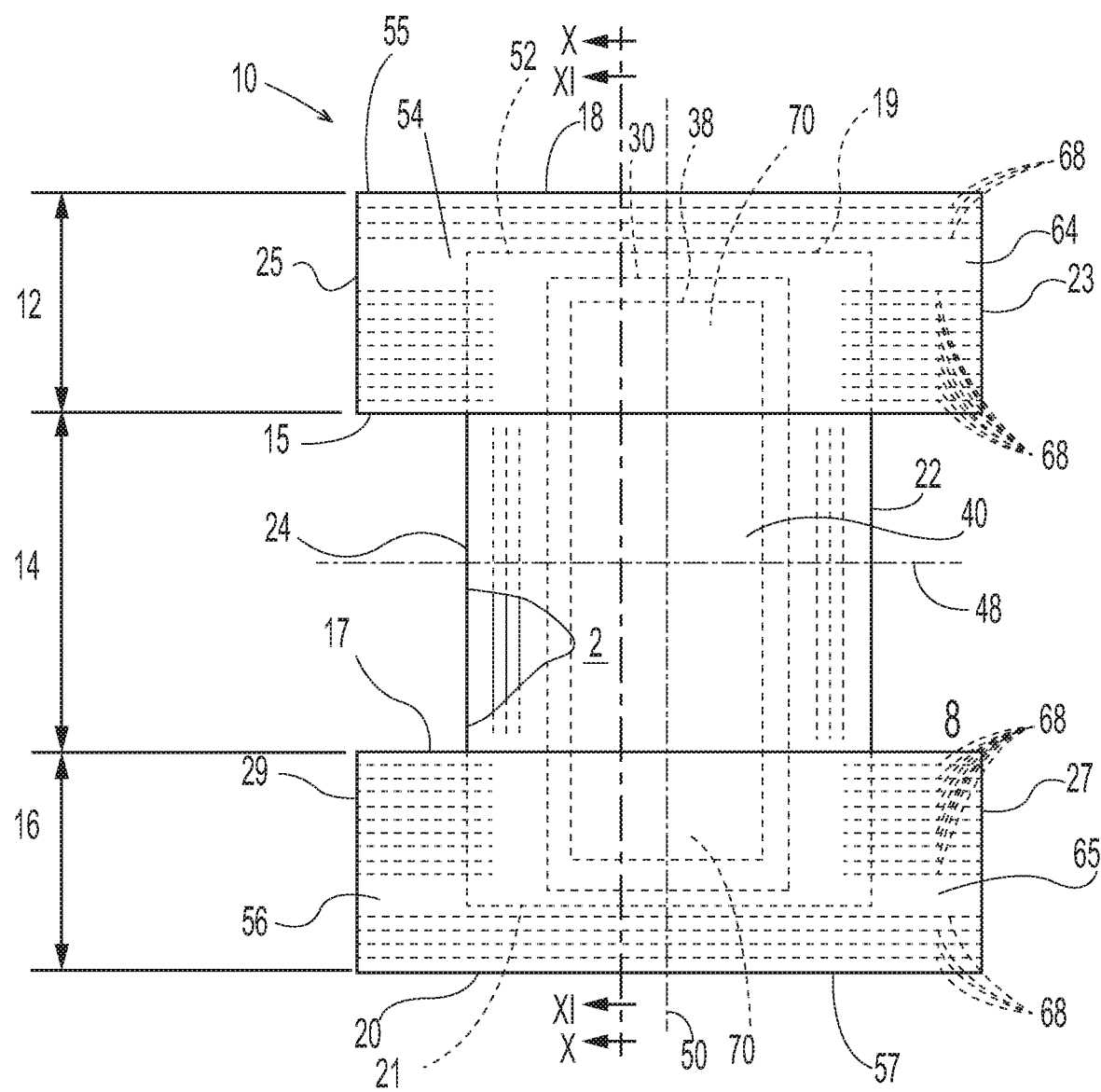
FIG. 8 is a plan view of the absorbent article of FIG. 6, laid flat, with a garment-facing surface facing the viewer.
Figure 9:
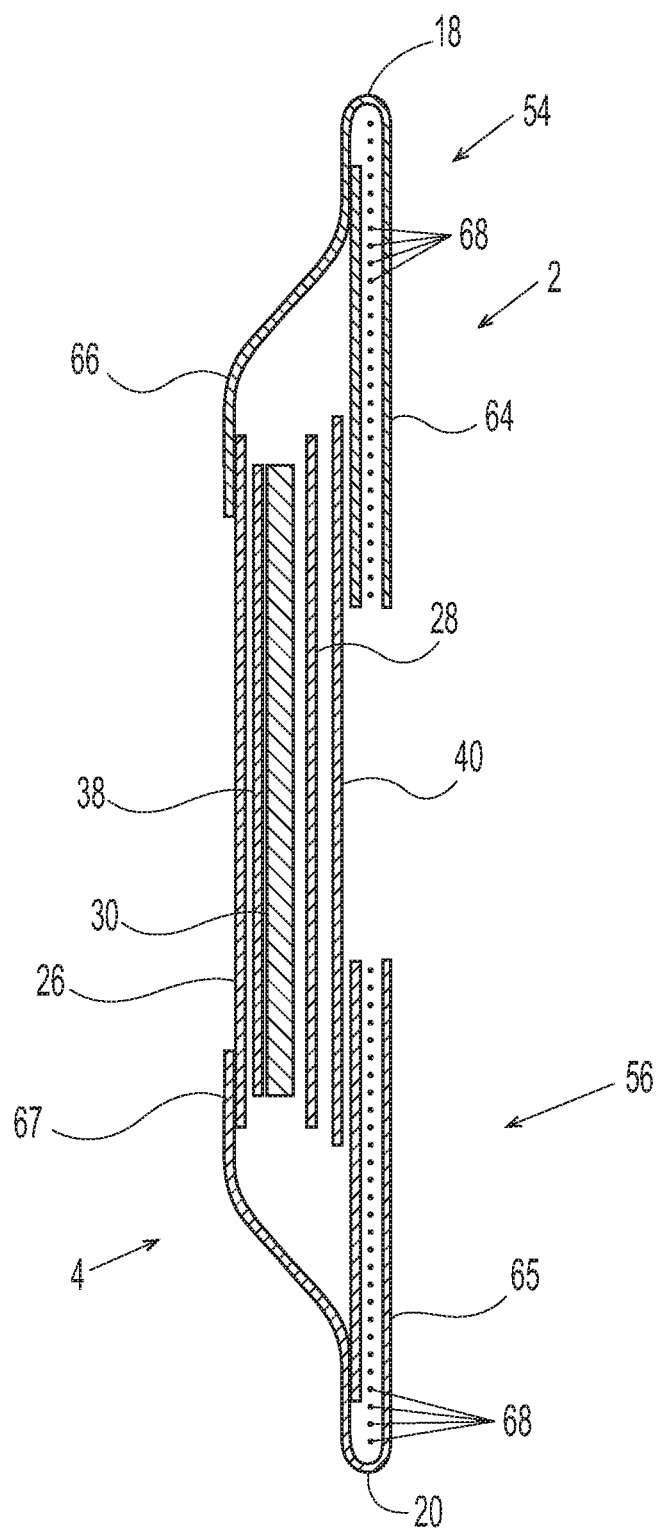
FIG. 9 is a cross-sectional view of the absorbent article taken about line IX-IX of FIG. 8.
Figure 10:
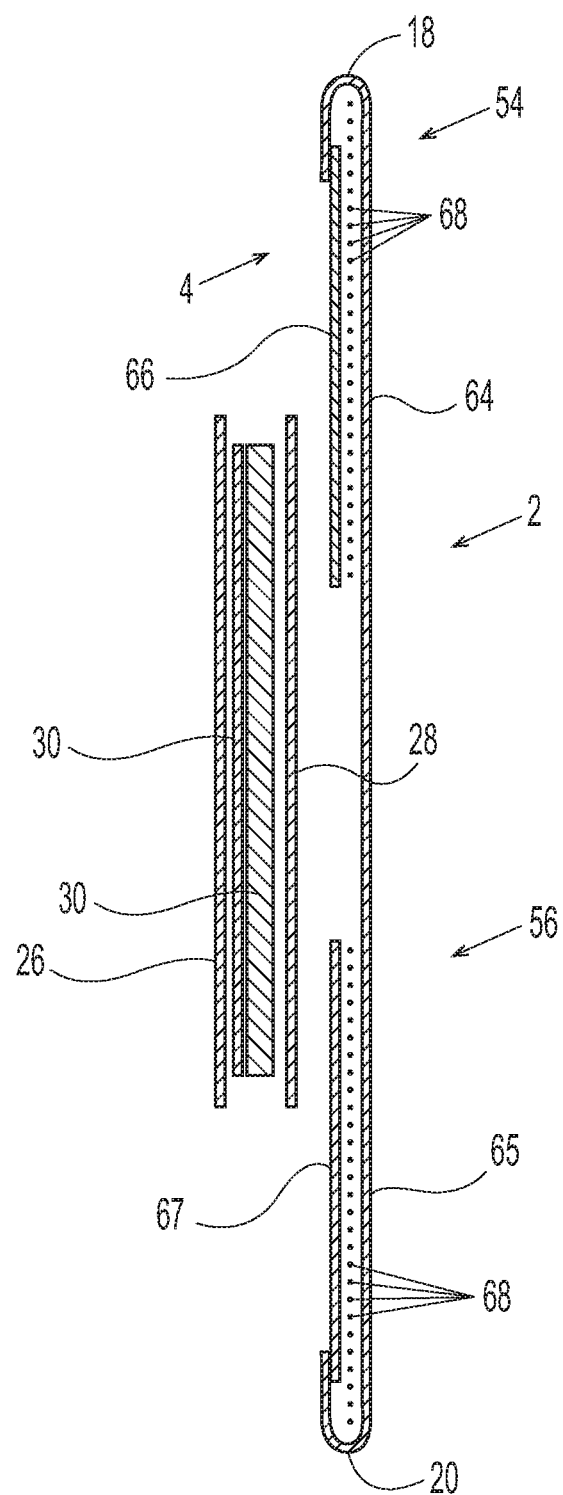
FIG. 10 is a cross-sectional view of the absorbent article taken about line X-X of FIG. 8.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 6-10, an example absorbent article 10 in the form of a pant is illustrated. FIG. 6 is a front perspective view of the absorbent article 10. FIG. 7 is a rear perspective view of the absorbent article 10. FIG. 8 is a plan view of the absorbent article 10, laid flat, with the garment-facing surface facing the viewer. Elements of FIG. 6-10 having the same reference number as described above with respect to FIGS. 3-5 may be the same element (e.g., absorbent core 30). FIG. 9 is an example cross-sectional view of the absorbent article taken about line IX-IX of FIG. 8. FIG. 10 is an example cross-sectional view of the absorbent article taken about line X-X of FIG. 8. FIGS. 9 and 10 illustrate example forms of front and back belts 54, 56. The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIGS. 3-5. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

A. Belts

Referring to FIGS. 9 and 10, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or, may alternatively, run continuously across the absorbent core 30. The elastics elements 68 may have uniform or variable spacing therebetween in any portion of the belts. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363. Front and back belt end edges 55 and 57 may extend longitudinally beyond the front and back chassis end edges 19 and 21 (as shown in FIG. 8) or they may be co-terminus. The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 9 and a gap between the front and back inner belt layers 66 and 67 is shown in FIG. 10.

The front and back belts 54 and 56 may include slits, holes, and/or perforations providing increased breathability, softness, and a garment-like texture. Underwear-like appearance can be enhanced by substantially aligning the waist and leg edges at the side seams 58 (see FIGS. 6 and 7).

The front and back belts 54 and 56 may comprise graphics (see e.g., 78 of FIG. 3). The graphics may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No. 9,498,389 to create a more underwear-like article. The graphics may also be discontinuous.

Alternatively, instead of attaching belts 54 and 56 to the chassis 52 to form a pant, discrete side panels may be attached to side edges of the chassis 22 and 24. Suitable forms of pants comprising discrete side panels are disclosed in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744.

B. Topsheet

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured (FIG. 4, element 31), may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

C. Backsheet

The backsheet 28 is generally that portion of the absorbent article 10 positioned proximate to the garment-facing surface of the absorbent core 30. The backsheet 28 may be joined to portions of the topsheet 26, the outer cover material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

D. Outer Cover Material

The outer cover material (sometimes referred to as a backsheet nonwoven) 40 may comprise one or more nonwoven materials joined to the backsheet 28 and that covers the backsheet 28. The outer cover material 40 forms at least a portion of the garment-facing surface 2 of the absorbent article 10 and effectively "covers" the backsheet 28 so that film is not present on the garment-facing surface 2. The outer cover material 40 may comprise a bond pattern, apertures, and/or three-dimensional features.

E. Absorbent Core

Figure 11:
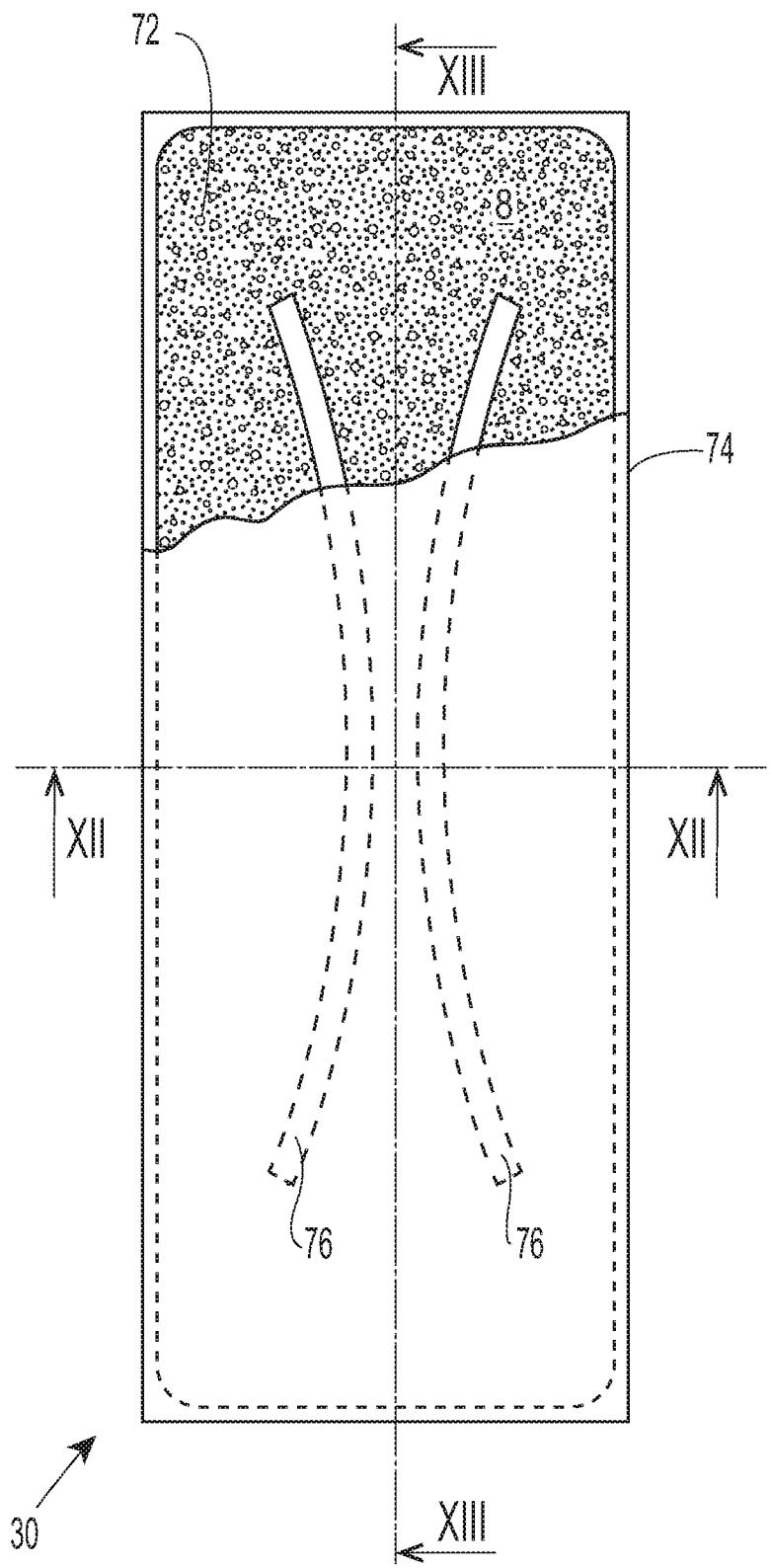
FIG. 11 is a plan view of an example absorbent core or an absorbent article.
Figure 12:
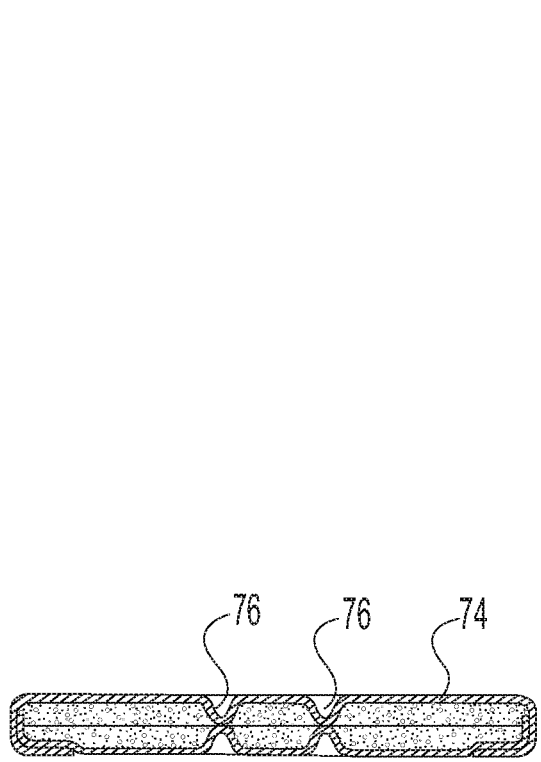
FIG. 12 is a cross-sectional view, taken about line XII-XII, of the absorbent core of FIG. 11.
Figure 13:
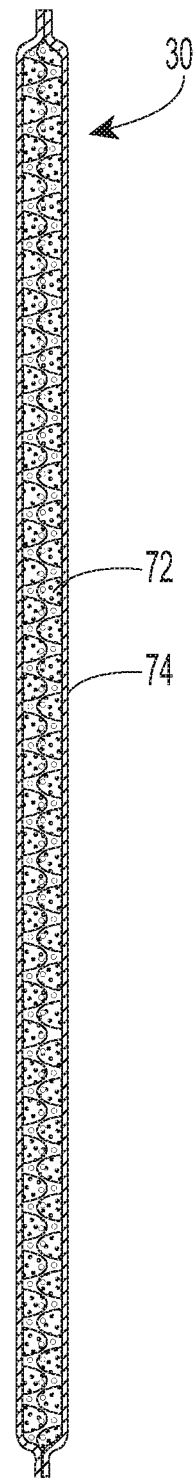
FIG. 13 is a cross-sectional view, taken about line XIII-XIII, of the absorbent core of FIG. 11.

As used herein, the term "absorbent core" 30 refers to the component of the absorbent article 10 having the most absorbent capacity and that comprises an absorbent material. Referring to FIGS. 11-13, in some instances, absorbent material 72 may be positioned within a core bag or a core wrap 74. The absorbent material may be profiled or not profiled, depending on the specific absorbent article. The absorbent core 30 may comprise, consist essentially of, or consist of, a core wrap, absorbent material 72, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 14 of the absorbent article 10.

Referring to FIGS. 11-13, the absorbent core 30 may have areas having little or no absorbent material 72, where a wearer-facing surface of the core bag 74 may be joined to a garment-facing surface of the core bag 74. These areas having little or no absorbent material may be referred to as "channels" 76. These channels can embody any suitable shapes and any suitable number of channels may be provided. In other instances, the absorbent core may be embossed to create the impression of channels. The absorbent core in FIGS. 11-13 is merely an example absorbent core. Many other absorbent cores with or without channels are also within the scope of the present disclosure.

F. Barrier Leg Cuffs/Leg Elastics

Referring to FIGS. 3 and 4, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body exudates approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14.

G. Elastic Waistband

Referring to FIGS. 3 and 4, the absorbent article 10 may comprise one or more elastic waistbands 36. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article.

H. Acquisition Materials

Referring to FIGS. 3, 4, 9, and 10, one or more acquisition materials 38 may be present at least partially intermediate the topsheet 26 and the absorbent core 30. The acquisition materials 38 are typically hydrophilic materials that provide significant wicking of bodily exudates. These materials may dewater the topsheet 26 and quickly move bodily exudates into the absorbent core 30. The acquisition materials 38 may comprise one or more nonwoven materials, foams, cellulosic materials, cross-linked cellulosic materials, air laid cellulosic nonwoven materials, spunlace materials, or combinations thereof, for example. In some instances, portions of the acquisition materials 38 may extend through portions of the topsheet 26, portions of the topsheet 26 may extend through portions of the acquisition materials 38, and/or the topsheet 26 may be nested with the acquisition materials 38. Typically, an acquisition material 38 may have a width and length that are smaller than the width and length of the topsheet 26. The acquisition material may be a secondary topsheet in the feminine pad context. The acquisition material may have one or more channels as described above with reference to the absorbent core 30 (including the embossed version). The channels in the acquisition material may align or not align with channels in the absorbent core 30. In an example, a first acquisition material may comprise a nonwoven material and as second acquisition material may comprise a cross-linked cellulosic material.

I. Landing Zone

Referring to FIGS. 3 and 4, the absorbent article 10 may have a landing zone area 44 that is formed in a portion of the garment-facing surface 2 of the outer cover material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa.

Absorbent article 10 may optionally employ a second landing zone area 95, as shown on FIG. 3, for sensor device attachment. Landing zone area 95 may comprise a discrete strip of material that is affixed to garment-facing surface 2. For example, a discrete fibrous strip of material may be used to engage hooks on an article-facing surface of the sensor device. Landing zone area 95 may comprise alternative engagement features, such as, for example, a pocket for partially or completely receiving the sensor device. It should be understood that the sensor device may be attachable directly to outer cover material 40 without the need for an additional strip of material or other landing zone component.

J. Wetness Indicator/Graphics

Referring to FIG. 3, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30 and thereafter change in visual appearance (for example, change color via pH sensitive materials). In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Graphic 82 is an optional target graphic for aiding a consumer in attaching a sensor device to absorbent article 10. FIG. 3 shows graphic 82 is proximate to but spaced apart from wetness indicator 80, but it can alternatively be adjacent to and/or overlap with indicator 80 depending on the size and configuration of a chosen sensor device.

K. Front and Back Ears

Referring to FIGS. 3 and 4, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic film or elastic strands may be positioned intermediate a first nonwoven material and a second nonwoven material. The elastic film may or may not be apertured. The ears may be shaped. The ears may be integral (e.g., extension of the outer cover material 40, the backsheet 28, and/or the topsheet 26) or may be discrete components attached to a chassis 52 of the absorbent article on a wearer-facing surface 4, on the garment-facing surface 2, or intermediate the two surfaces 4, 2.

II. Data Gathering Module

The data gathering module comprises the sensor device. The sensor device can be a single-use device, or a multi-use device that is attachable to and detachable from a disposable absorbent article (such as absorbent article 10 shown in FIGS. 3-8) or article of clothing worn by an individual. When the sensor device is a single-use device it may come already associated with a purchased absorbent article or it may be attachable by a wearer or caregiver.

The sensor device includes a sensor housing that generally protects sensors and other electronic components disposed therein, as well as inhibiting unwanted contact of the same with an infant, patient, or caregiver. The housing can be made from a variety of materials, both flexible and rigid, examples of which include thermoplastic polymers, thermoplastic elastomers, silicone, Tecaform, Tecanant, and combinations thereof. Other materials can also be employed for the housing so long as it is generally regarded as safe for human contact and does not cause irritation or other unwanted health effects. Inclusion of a bittering agent or other approaches may optionally be used to discourage placement of the sensor device in one's mouth or otherwise tampering with the sensor device.

The sensor device may be attachable to skin (via hydrogel or bio-adhesive material, for example), to a disposable article such as an absorbent article defined herein, and/or to clothing worn by an individual. Various attachment mechanisms may be employed for attaching the sensor device to an article of clothing or an absorbent article. For example, hook and loop fastening mechanisms, magnets, adhesives, thermal bonds, and male and female mating fasteners such as snaps and buttons. Receiving features, such as pockets, recesses, and voids may also be employed that essentially hold the sensor device with or without attachment features.

In yet another form, an auxiliary article may be used to integrate the sensor device with an absorbent article. The auxiliary article may be in the form of a pant-like reusable garment designed to fit over an absorbent article. Such auxiliary articles may include inexpensive, stretchable materials including, for example, rayon, nylon, polyester, polyolefins, spandex, cotton, wool, and combinations thereof.

In one form, the sensor device is adapted for attachment to the outer cover of an absorbent article. Hook and loop features can be used with this attachment approach. For example, a strip of hook material can be affixed to one surface of the sensor housing, where the hooks can engage directly with material used for the outer cover or with an added strip of material, such as landing zone 95 shown in FIG. 3.

The sensor housing comprises a plurality of electronic component disposed on and/or within the housing. Typically, the electronic components include at least one sensor, a transmitter, and a power source (e.g., a disposable battery or a rechargeable battery). The number and type of sensors employed by the sensor device are chosen based on the application of the systems and methods disclosed herein. Exemplary sensors include, but are not limited to, optical sensors, color sensors, wetness sensors, BM (bowel movement) sensors, motion sensors, temperature sensors, chemical sensors, strain gauges, and combinations thereof. A VOC (volatile organic compound) sensor is one suitable type of a BM sensor. And a triaxial accelerometer (typically measuring linear movement/motion) is one suitable type of motion sensor. Alternative or additional motion sensors can be used, including, for example, inertial measurement units (IMUs), gyroscopes for measuring angular movements, and magnetometer for measuring magnetic fields. The VOC sensors can be of MOS-type (metal oxide). BM sensors can be capable of acting as an electronic nose to detect chemical signatures of organic materials associated with body exudates, including, for example, skatole, mercaptans, amines, volatile fatty acids, acetone, methyl acetate, and methanol. BM sensors may also include leverage an optical or color sensor to detect the presence of feces in the article. Along these lines, multiple optical or color sensors can be used to detect both urine and feces, based either on their inherent colors or based on use of an indicator that changes color in the presence of urine and/or feces. For example, the following enzymes associated with body exudates can trigger an optical change in an included indicator that can be sensed by an optical or color sensor: urease, trypsin, chemotrypsin, LAP, lipase, amilase, and urease.

Wetness sensors for detecting the presence of urine or other bodily fluid can include optical sensors, color sensors, and electrical sensors that comprise a resistance, capacitance, inductance or continuity sensitive indicator. A resistance sensitive indicator can be provided, for example, by providing two electrical conductors disposed at a given spatial distance relative to each other.

Figure 14:
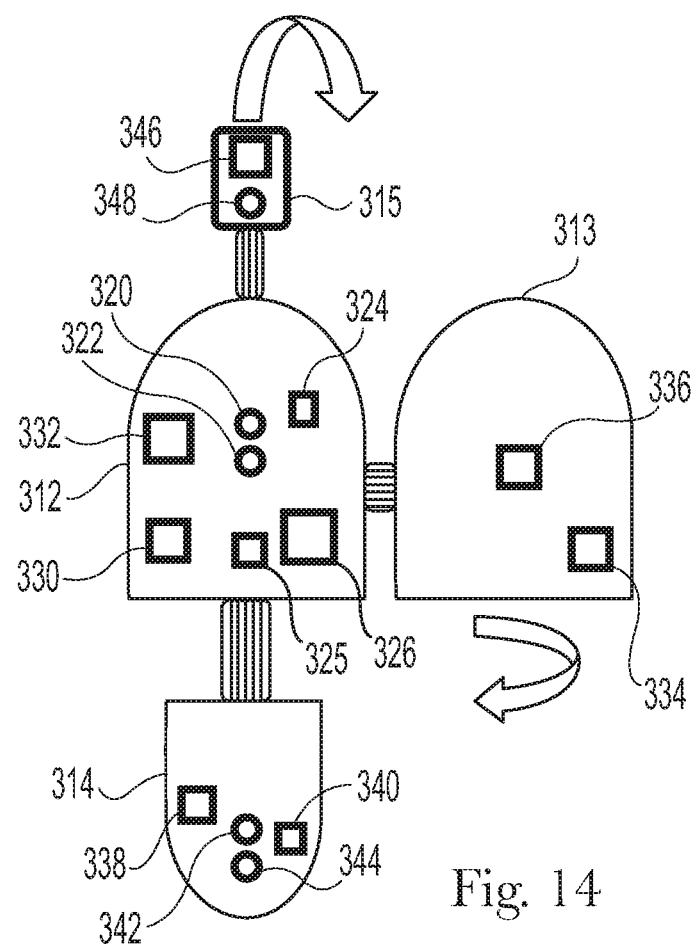
FIG. 14 is a partial view of an exemplary sensor device of the present disclosure.
Figure 15:
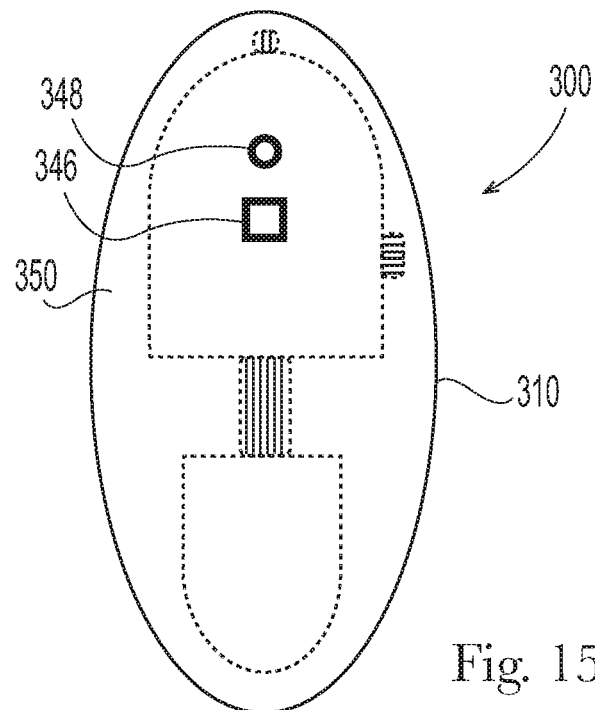
FIG. 15 is a caregiver-facing side of a sensor device of the present disclosure.

FIGS. 14 and 15 illustrate aspects of one exemplary sensor device 300 comprising a plurality of sensors and other electronic components. FIG. 14 shows the sensor device in a manufactured form before its final configuration and encasing with a sensor housing 310 (shown in FIG. 15). With reference to FIG. 14, multiple electrically-connected printed circuit boards 312, 313, 314, and 315 are employed. Printed circuit board 312 comprises an optical sensor 320, an absorbent article-facing light source 322, a power management component 324, a flash memory component 326, an optical sensor frontend 328, a processor and transmitter component 330, and an antenna 332. Printed circuit board 313 comprises a motion sensor (e.g., accelerometer) 334 and a power source (e.g., coin cell battery) 336. Printed circuit board 314 comprises a BM sensor (e.g., VOC sensor) 338, a temperature and relative humidity sensor 340, a second optical sensor 342, and a second absorbent article-facing light source 344. And printed circuit board 315 comprises a consumer-engageable button 346 for activating or otherwise operating sensor device 300, and a caregiver-facing light source 348 to indicate an operational aspect of sensor device 300. Button 346 or similar engageable feature can be used for multiple tasks. For example, button 346 can be initially activated for "waking" the sensor up from a power-save mode and/or manually activated by a caregiver upon changing an absorbent article if a wearer of the article has had a bowel movement. Acknowledgement of a bowel movement via action of button 346 or similar engageable feature can be communicated by the sensor device to a communication module for tracking timing, frequency, or other aspects of a wearer's bowel movement history. One skilled in the art would appreciate that a single circuit board can be employed in a sensor device, as well as other numbers of circuit boards beyond what is shown in FIG. 14.

FIG. 14 includes two arrows showing how exemplary sensor device 300 is manipulated, with circuit boards 313 and 315 being folded over onto circuit board 312 before sensor housing 310 is added as shown in FIG. 15. The caregiver-facing surface 350 is shown in FIG. 15, wherein button 346 is and light source 348 are visible.

Figure 16:
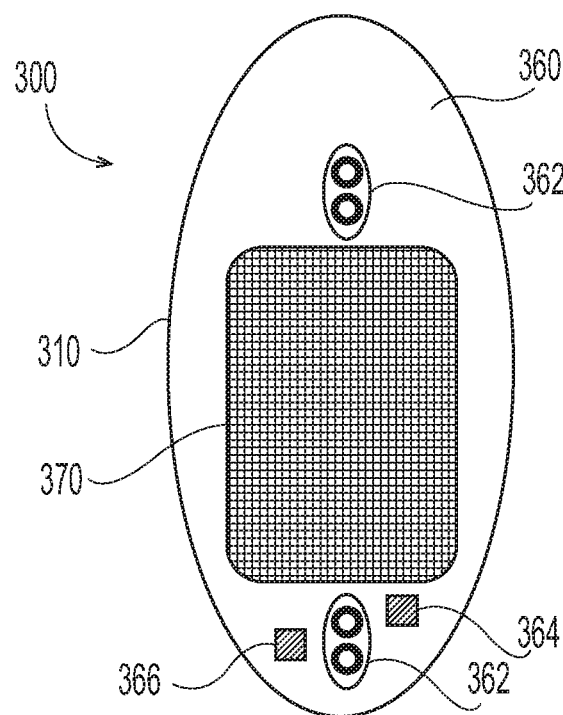
FIG. 16 is a disposable article-facing side of the sensor device of FIG. 15.

FIG. 16 shows article-facing surface 360 of sensor device 300. Note that internal components are not shown in FIG. 16 like they were in FIG. 15. Instead, FIG. 16 illustrates windows 362 in sensor housing 310 to permit the pairs of light sources 322, 344 and optical sensors 320, 342 to operate properly, particularly when sensor housing 310 is opaque. Article-facing surface 360 also includes a port 364 for BM sensor 338, and a port 366 for temperature a relative humidity sensor 340 to operate properly. Lastly, exemplary sensor device 300 includes a patch of hook material 370 for engaging fibrous material on a disposable absorbent article.

Many prior art systems that included more than one sensor type would employ individual sensor housings for each of the sensor types. This can be disadvantageous, as it can require attachment and detachment of multiple items from an article, which is cumbersome and can increase errors. Thus, integrating multiple sensors into a single sensor housing can be highly desirable. However, the overall size or footprint of such a sensor housing can become large as functionality increases. And while a relatively large sensor device and accompanying sensor housing is okay for attachment to an article of clothing like a onesie, the available area for attachment to a small size disposable absorbent article (e.g., newborn size, or size 1 or 2 diaper) is quite limited. In some forms of the present disclosure, the sensor device comprises a transmitter, a battery, and three, four, five or more sensors within a single sensor housing that is attachable within an absorbent article area of 25 $cm^2$ or 20 $cm^2$ or less. This area or sensor "footprint" can be determined a number of different ways, including attaching the sensor to an absorbent article, drawing a line around the perimeter of the sensor with a marker, removing the sensor, and then conducting image analysis to determine the area within the drawn line. In these or other forms of the present disclosure, center-to-center distances between adjacent electronic components within the sensor housing is no more than 2.0 cm, 1.5 cm, 1.0 cm, 0.8 cm, or 0.5 cm. In yet other forms, the distance between attachment points of adjacent electronic components to a printed circuit board or other substrate can be no more than 20 mm, 10 mm, 8 mm, 5 mm, 4 mm, 3 mm, or 2 mm.

While it can be advantageous to employ as many different electronic components within a given area/volume to increase sensor device functionality, at least some of the sensor devices of the present disclosure are removable from an absorbent article. And if removable, the sensor device must comply with safety regulations including small part regulations for products marketed for use with infants and minors. Choking is one of the concerns with products in this marketing space. United States 16 Code of Federal Regulation ("CFR") 1501.4 defines a cylinder test apparatus, and products must be able to fit entirely within this test cylinder to comply with regulations. Some sensor devices described herein have multiple monitoring capabilities, but are sized and configured so as not to fit entirely within the cylinder test apparatus. For safety and convenient handling of the sensor device, it may be useful that the sensor device in applications with infants has a length of at least 3 cm, 4 cm, 5 cm, 6 cm, 7 cm, 8 cm, or more, and normally less than 15 cm and a width of at 1 cm, 2 cm, 3 cm, or 4 cm, and normally less than 8 cm. Exemplary sensor device thicknesses are those from about 0.2 cm to about 1.5 cm. For applications with toddlers or adults, the dimensions of the sensor device may be the same or larger.

In one form, the sensor device comprises a power source in the form of a battery, a transmitter, multiple optical sensors (e.g., a color sensor), multiple light sources (e.g., an LED), an accelerometer, and optionally a VOC sensor. The sensor device is attached to an absorbent article comprising a wetness indicator, as described above, such that the light source can direct light onto the wetness indicator. The wetness indicator changes appearance (e.g., changes color) when a wearer urinates into the absorbent article. The optical sensor measures the reflected light from the wetness indicator to sense when a urination event occurs. Multiple pairs of absorbent article-facing light sources and optical sensors can be employed to sense changes of a wetness indicator at different points along the indicator to confirm a urination event has occurred, or predict the volume of urine and/or number of urination events that occurred. A signal from the optical sensor can then be transmitted to the data processing module. The accelerometer is employed to track data associated with sleep and awake times. The awake data can include awake feeding motion data and awake non-feeding motion, and the inventors have discovered how to distinguish the two. The accelerometer is capable of sensing breastfeeding times and provide feeding information for one's right breast and left breast. And the optional VOC sensor can sense a bowel movement and communicate a signal indicating the same via the transmitter.

The data gathering module may also contain secondary devices that while not necessarily intimately associated with an infant or patient, can obtain data and information regarding the status of the infant/patient and/or their environment, and/or impact their environment. By way of example only, the data gathering module may contain a camera, a light source, an audio device (comprising a speaker and/or microphone), a carbon monoxide sensor, a smoke detector, humidity device, and temperature device.

III. Data Processing Module

The data processing module can comprise data transmission, data storage, data interpretation, data filtering, and/or data manipulation to transform the data from the data gathering module into consumer understandable information related to the wellbeing of an individual, including, for example, feeding, sleeping, and/or voiding. The data processing module can include algorithms to parse/filter the received data. Data processing can be accomplished by one or more devices and in the same or different locations. For example, the sensor device may optionally employ a memory device to temporarily store data. One reason for temporary storage of data is when communication between the sensor device and a remote data processing module component and/or the information communication module is unavailable.

The sensor device may also optionally employ a data processor for processing raw data from one or more sensors associated with the sensor device prior to transmitting data/information based on the raw data. This can reduce the volume of data/information transmitted from the sensor device, and thereby reduce the amount of power required and accompanying electromagnetic radiation emission.

IV. Information Communication Module The communication module comprises a software application operable on a computer device to display information related to the data obtained by the data gathering module, including data transformed via the data processing module. The computer device may be a smart phone, as is shown in FIG. 2, but other computer devices, such as a laptop, tablet, digital assistant (ALEXA and GOOGLE HOME, for example) can be used to communicate information to one or more caregivers.

V. Systems and Kits

Sensor devices and systems including the same can form a part of consumer purchasable kit. One exemplary kit includes two or more sensor devices as described herein, a camera, a plurality of absorbent articles that can accept the sensor devices, and access to a software application for viewing data and information flowing from the sensor device and any other secondary data gathering device(s). A subscription can also be offered to consumers that provides delivery of additional absorbent articles, sensor devices, and/or continued access and operation of the software application. For example, a subscription can include an automatic delivery of a number of absorbent articles every two weeks along with a code or other mechanism for continued operation of the software application. The subscription can work with an affirmative action request by a consumer or as an automatic delivery order that delivers products on a set re-occurring schedule until the schedule reaches a predetermined endpoint, or is altered or discontinued by the consumer. Similar to the subscription example above, packages of absorbent articles can be sold in brick and mortar locations wherein the packages contain a code for operation of the software application to view data and information received from a sensor device according to the present disclosure.

Figure 17:
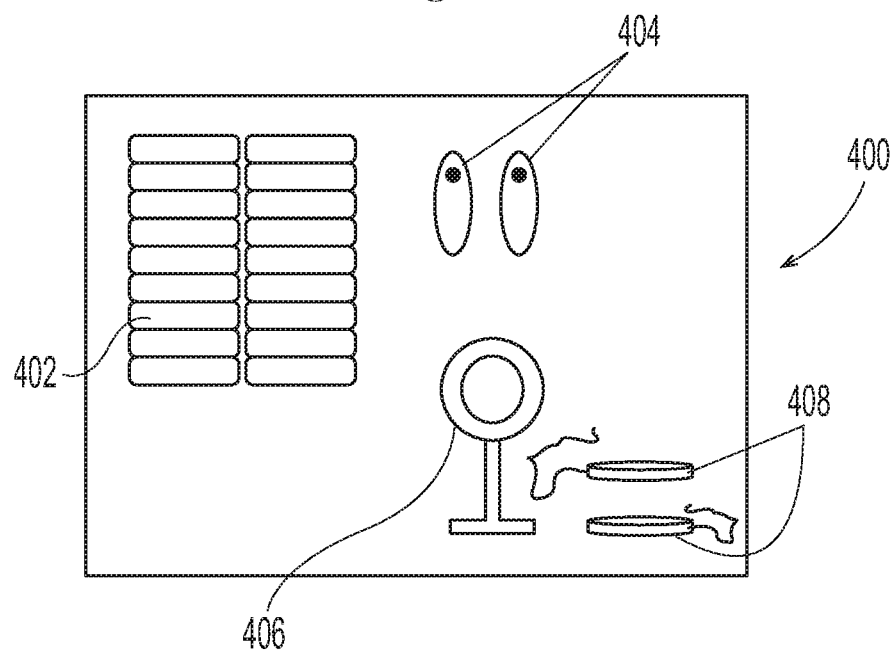
FIG. 17 is an exemplary kit of the present disclosure, comprising a plurality of disposable absorbent articles, two sensor devices, a camera, and two camera docking stations.

FIG. 17 shows an exemplary kit 400 comprising a plurality of absorbent articles 402, two sensor devices 404, a camera 406, and two camera docking stations 408.

Sensor devices by themselves may also be offered for sale, which would include information on how to associate the sensor device with a disposable absorbent article.

While the discussion has focused on infants and patients, systems of the present invention are also applicable for elderly care. The sensors associated with such systems may be capable of association with an elderly's skin, durable undergarments, disposable absorbent articles, bed materials, bed pads, and/or clothing articles.

This application is a continuation of U.S. application Ser. No. 16/402,348, filed on May 3, 2019, which claims the benefit of U.S. Provisional Application No. 62/723,179, filed on Aug. 27, 2018 and 62/666,989, filed on May 4, 2018, the entireties of which are all incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any disclosure disclosed or claimed herein or that it alone, or in any combination with any other reference or references, teaches, suggests or discloses any such disclosure. Further, to the extent that any meaning or definition of a term in this document conflicts with any meaning or definition of the same term in a document incorporated by reference, the meaning or definition assigned to that term in this document shall govern.

While particular forms of the present disclosure have been illustrated and described, it would be obvious to those skilled in the art that various other changes and modifications can be made without departing from the spirit and scope of the disclosure. It should be understood that other forms may include more or less of each element shown in a given figure. Further, some of the illustrated elements may be combined or omitted. Yet further, an exemplary form may include elements that are not illustrated in the figures. The various aspects and forms disclosed herein are for purposes of illustration and are not intended to be limiting, with the true scope and spirit being indicated by the following claims.

What is claimed is:

1. A system for monitoring the basic needs of an infant, the system comprising:
   a. a multi-use sensor device having hooks configured for attachment to and detachment from an outer cover of a disposable absorbent article, the multi-use sensor device comprising a bowel movement event sensor which is a volatile organic compound sensor capable of detecting at least one of the following: skatole, mercaptans, amines, volatile fatty acids, acetone, methylacetate and methanol, and optionally a urination event sensor;
   b. a plurality of disposable absorbent articles for receiving the multi-use sensor device, each of the plurality of absorbent articles comprising a backsheet comprising a film that is liquid impermeable but that is breathable in that it allows vapors of said volatile organic compounds to escape from the absorbent articles, thereby allowing detecting by said bowel movement event sensor, and an outer cover material comprising a nonwoven layer providing loops, said article comprising a target graphic to show a landing zone area which aids a consumer to temporarily attach the hooks of the sensor device to the loops of the outer cover material;
   c. a software application that is operable on a computer device to display information related to data obtained by the multi-use sensor device; and
   d. a subscription providing delivery of additional absorbent articles and multi-use sensor devices; and
   e. wherein said system for monitoring further comprise a data management system which receives data from said sensor device and data management system having one or more relationship models that allow a primary caregiver of said infant to provide access to some or all of said data to secondary care providers; and
   f. wherein the sensor device includes a bittering agent that discourages placement of the sensor device in one's mouth.

2. The system of claim 1, wherein delivery of the additional absorbent articles and multi-use sensor devices requires an affirmative request by a consumer with access to the subscription.

3. The system of claim 1, wherein delivery of the additional absorbent articles and multi-use sensor devices is automatic according to a set re-occurring schedule.

4. The system of claim 1, comprising two multi-use sensor devices.

5. The system of claim 1, wherein the multi-use sensor device comprises a temperature sensor.

6. The system of claim 1, wherein the multi-use sensor device comprises a humidity sensor.

7. The system of claim 1, wherein the multi-use sensor device comprises a volatile organic compound sensor, a temperature sensor, and a humidity sensor.

8. The system of claim 1, wherein the multi-use sensor device comprises a motion sensor.

9. The system of claim 8, wherein the motion sensor comprises an accelerometer.

* * * * *